(12) United States Patent
Ganapathy et al.

(10) Patent No.: US 10,813,905 B2
(45) Date of Patent: Oct. 27, 2020

(54) METHODS OF TREATING SICKLE CELL DISEASE AND RELATED DISORDERS USING FUMARIC ACID ESTERS

(71) Applicant: Augusta University Research Institute, Inc., Augusta, GA (US)

(72) Inventors: Vadivel Ganapathy, Martinez, GA (US); Pamela M. Martin, Evans, GA (US)

(73) Assignee: Augusta University Research Institute, Inc., Augusta, GA (US)

( * ) Notice: Subject to any disclaimer, the term of this patent is extended or adjusted under 35 U.S.C. 154(b) by 0 days.

(21) Appl. No.: 15/666,393

(22) Filed: Aug. 1, 2017

(65) Prior Publication Data

US 2017/0333378 A1 Nov. 23, 2017

Related U.S. Application Data

(63) Continuation of application No. 14/105,893, filed on Dec. 13, 2013, now abandoned.

(60) Provisional application No. 61/737,360, filed on Dec. 14, 2012.

(51) Int. Cl.
*A61K 31/225* (2006.01)
*A61K 31/17* (2006.01)

(52) U.S. Cl.
CPC .......... *A61K 31/225* (2013.01); *A61K 31/17* (2013.01)

(58) Field of Classification Search
USPC ....................................... 514/547
See application file for complete search history.

(56) References Cited

U.S. PATENT DOCUMENTS

| | | |
|---|---|---|
| 4,959,389 A | 9/1990 | Speiser et al. |
| 5,939,456 A | 8/1999 | Perrine |
| 6,011,000 A | 1/2000 | Perrine et al. |
| 6,277,882 B1 | 8/2001 | Joshi et al. |
| 6,355,676 B1 | 3/2002 | Joshi et al. |
| 6,436,992 B1 | 8/2002 | Joshi et al. |
| 6,509,376 B1 | 1/2003 | Joshi et al. |
| 2004/0054001 A1 | 3/2004 | Joshi et al. |
| 2008/0004344 A1 | 1/2008 | Nilsson et al. |
| 2008/0299196 A1 | 12/2008 | Nilsson et al. |
| 2010/0048651 A1 | 2/2010 | Gangakhedkar et al. |
| 2012/0095003 A1 | 4/2012 | Gangakhedkar et al. |
| 2012/0157523 A1 | 6/2012 | Gangakhedkar et al. |
| 2012/0165404 A1 | 6/2012 | Lukashev |
| 2014/0171504 A1 | 6/2014 | Ganapathy et al. |
| 2014/0356458 A1 | 12/2014 | Essack et al. |
| 2016/0074355 A1 | 3/2016 | Ganapathy et al. |

FOREIGN PATENT DOCUMENTS

| | | |
|---|---|---|
| EP | 2137537 B1 | 5/2013 |
| EP | 2137537 B8 | 6/2016 |
| WO | WO 2008097596 A2 | 8/2008 |

OTHER PUBLICATIONS

Aliyu et al., "Current therapy of sickle cell disease", Haematologica, 91(1):7-10 (2006).
Belcher et al., "Activated monocytes in sickle cell disease: potential role in the activation of vascular endothelium and vaso-occlusion", Blood, 96(7):2451-2459 (2000).
Crossman, "XeonoPort reports favorable metabolism and pharmacokinetics of xp23829, a novel fumaric acid ester, in phase 1 trail", http://investor.xenoport.com/releasedetail.cfm?releaseid=711332, retreived Nov. 8, 2012.
Fox, "BG00012—A novel oral therapy in development for the treatment of multiple sclerosis", Eu Neurological Rev., Thouch Briefings 99-103 (2008).
Gilmore et al., "Inhibitors of NF-kappaB signaling: 785 and counting", Oncogene, 25(51):6887-6899 (2006).
Hemoglobinopathies: Sickle Cell Disease (HbSS, HbSC or HbS/β-Thalassemia), Newborn Screening Program (2006).
In re Sullivan, 498 F.3d 1345 (Fed. Cir. 2007).
Kollander et al., "Nuclear factor-kappa B (NFkappaB) component p50 in blood mononuclear cells regulates endothelial tissue factor expression in sickle transgenic mice: implications for the coagulopathy of sickle cell disease", Transl Res., 155(4):170-177 (2010).
Kreuter et al., "Treatment of disseminated granuloma annulare with fumaric acid esters", BMC Dermatol, 2:5 (2002).
Litjens et al., "Pharmacokinetics of oral fumarates in healthy subjects", Br J Clin Pharmacol, 58(4):429-432 (2004).
Liu et al., "Hemoglobin induction in mouse macrophages", Proc Natl Acad Sci USA, 96(12):6643-6647 (1999).
Makala et al., "FK228 Analogues Induce Fetal Hemoglobin in Human Erythroid Progenitors", Anemia, 2012:428137 (2012).
Nast et al., "German S3-guidelines on the treatment of psoriasis vulgaris", J. German Soc. Dermatol, 4:51-55 (2006).
Newton et al., "Hemoglobin is expressed by alveolar epithelial cells", J Biol Chem., 281(9):5668-5676 (2006).
Ngan, "Fumaric acid esters", DermNet NZ, http://dermnetnz.org/treatments/fumaric-acid-esters.html, retrieved from internet Nov. 5, 2012.
Promsote et al., "Monomethylfumarate induces γ-globin expression and fetal hemoglobin production in cultured human retinal pigment epithelial (RPE) and erythroid cells, and in intact retina", Invest Ophthalmol Vis Sci., 55(8):5382-5393 (2014).

(Continued)

*Primary Examiner* — Kathrien A Cruz
(74) *Attorney, Agent, or Firm* — Jones Day

(57) ABSTRACT

Methods of using one or more fumaric acid esters or pharmacologically active salts, derivatives, analogues, or prodrugs thereof to increase expression of fetal hemoglobin (HbF) are disclosed. The methods typically include administering to a subject an effective amount of one or more fumaric acid esters optionally in combination or alternation with hydroxyurea to induce HbF expression in the subject in an effective amount to reduce one or more symptoms of a sickle cell disorder, a hemoglobinopathy, or a beta-thalassemia, or to compensate for a genetic mutation is the human beta-globin gene (HBB) or an expression control sequence thereof. Pharmaceutical dosage units and dosage regimes for use in the disclosed methods are also provided.

12 Claims, 11 Drawing Sheets

(56) References Cited

OTHER PUBLICATIONS

Promsote et al., "Oral Monomethyl Fumarate Therapy Ameliorates Retinopathy in a Humanized Mouse Model of Sickle Cell Disease", Antioxid Redox Signal, Epub ahead of print, Aug. 22, 2016.
Roll et al., "Use of fumaric acid esters in psoriasis", Indian J Dermatol Venereol Leprol, 73(2):133-137 (2007).
Rowley, "The diagnosis of beta-thalassemia trait: a review", Am J Hematol, 1(1):129-137 (1976).
Schimrigk et al., "Oral fumaric acid esters for the treatment of active multiple sclerosis: an open-label, baseline-controlled pilot study", Eur J Neurol., 13(6):604-610 (2006).
Tezel et al., "Synthesis and secretion of hemoglobin by retinal pigment epithelium", Invest Ophthalmol Vis Sci., 50(4):1911-1919 (2009).
Walker et al., "Transcellular movement of hydroxyurea is mediated by specific solute carrier transporters", Exp Hematol, 39(4):446-456 (2011).
XenoPort, "XenoPort Reports Favorable metabolism and Pharmacokinetics of XP23829, a Novel Fumaric Acid Ester, in Phase 1 Trial", Santa Clara, CA (2012).
Bovenschen et al., "Dimethylfumarate for psoriasis: Pronounced effects on lesional T-cell subsets, epidermal proliferation and differentiation, but not on natural killer T cells in immunohistochemical study", Am J Clin Dermatol, 11(5):343-350 (2010).
Platt, "Hydroxyurea for the treatment of sickle cell anemia", N Engl J Med., 358(13):1362-1369 (2008).
Sharma et al., "Hydroxyurea as an alternative therapy for psoriasis", Indian J Dermatol Venereol Leprol, 70(1):13-17 (2004).
Balasubramaniam et al., "Fumaric acid esters in severe psoriasis, including experience of use in combination with other systemic modalities", Br J Dermatol, 150(4):741-746 (2004).
Macari et al., "Induction of human fetal hemoglobin via the NRF2 antioxidant response signaling pathway", Blood. 117(22):5987-5997 (2011).
Macari et al., "Simvastatin and t-butylhydroquinone suppress KLF1 and BCL11A gene expression and additively increase fetal hemoglobin in primary human erythroid cells", Blood, 121(5):830-839 (2013) (prepublished online as Blood First Edition paper, Jan. 5, 2012).
Office Action for U.S. Appl. No. 14/939,623 dated Jun. 29, 2016.
Office Action for U.S. Appl. No. 14/939,623 dated Jan. 24, 2017.
Office Action for U.S. Appl. No. 14/105,893 dated Feb. 24, 2015.
Office Action for U.S. Appl. No. 14/105,893 dated Sep. 1, 2015.
Office Action for U.S. Appl. No. 14/105,893 dated May 16, 2016.
Office Action for U.S. Appl. No. 14/105,893 dated Feb. 6, 2017.
Assessment Report TECIFDERA®, published by the European Medicines Agency, Nov. 26, 2013, 136 pages.
Nieboer et al 1989, "Systemic therapy with fumaic acid derivates: New possibilities in the treatment of psoriasis," Journal of the American Academy of Dermatology, 20(4):601-607, Apr. 1989.
Nieboer et al 1990, "Fumaric Acid Therapy in Psoriasis: A Double-Blind Comparison between Fumaric Acid Compound Therapy and Monotherapy with Dimethylfumaric Acid Ester," Dermatologica, 181(1): 33-37.
Rostami-Yazdi et al. 2009, "Detection of Metabolites of Fumaric Acid Esters in Human Urine: Implications for Their Mode of Action," Journal of Investigative Dermatology, 129(1): 231-234, Aug. 2008.

FIGS. 5A-B

METHODS OF TREATING SICKLE CELL DISEASE AND RELATED DISORDERS USING FUMARIC ACID ESTERS

CROSS-REFERENCE TO RELATED APPLICATIONS

This application is a continuation of U.S. patent application Ser. No. 14/105,893, filed Dec. 13, 2013, which claims the benefit of U.S. Provisional Application No. 61/737,360, filed Dec. 14, 2012, each of which is incorporated by reference herein in its entirety.

STATEMENT REGARDING FEDERALLY SPONSORED RESEARCH OR DEVELOPMENT

This invention was made with government support under Agreement NEI EY018053 awarded the National Institutes of Health. The government has certain rights in the invention.

FIELD OF THE INVENTION

The field of the invention is generally related to compositions including fumaric acid esters and methods of their use for HbF (γ-globin gene) induction.

BACKGROUND OF THE INVENTION

Sickle-cell disease (SCD), also known as sickle-cell anemia (SCA) and drepanocytosis, is an autosomal recessive genetic blood disorder caused by a point mutation in the β-globin chain of hemoglobin. SCD is characterized by red blood cells that adopt an abnormal, rigid, sickle shape, referred to as "sickling" under low-oxygen conditions. Repeated episodes of sickling can damage the blood cell's membrane and decrease its elasticity. Sickled cells can fail to return to normal shape when normal oxygen tension is restored. As a consequence, these rigid blood cells are unable to deform as they pass through narrow capillaries, leading to vessel occlusion and ischemia. The actual anemia of the illness is caused by hemolysin, the destruction of the red cells, caused by their misshapes.

Normally, humans have Hemoglobin A, which consists of two alpha and two beta chains. Hemoglobin A2, which consists of two alpha and two delta chains and Hemoglobin F, consisting of two alpha and two gamma chains in their bodies. Of these, Hemoglobin A makes up around 96-97% of the normal hemoglobin in humans. Fetal hemoglobin (also hemoglobin F or HbF) is the main oxygen transport protein in the fetus during the last seven months of development in the uterus and in the newborn until roughly six months old. Functionally, fetal hemoglobin differs most from adult hemoglobin in that it is able to bind oxygen with greater affinity than the adult form, giving the developing fetus better access to oxygen from the mother's bloodstream.

In newborns, fetal hemoglobin is nearly completely replaced by adult hemoglobin by approximately six months postnatally. However, HbF can be reactivated pharmacologically, an approach that has been investigated as a treatment for symptoms and complications of SCD.

Several classes of pharmacological agents that reactive γ-globin gene transcription, thereby inducing HbF production, have been identified. However, the S-stage cytotoxic drug hydroxyurea (HU) is the first and at present only FDA-approved drug for treatment of SCD. While HU has been shown to reduce vaso-occlusive episodes and associated complications such as pain and acute chest episodes in a large number of sickle-cell patients treated, there are a number of limitations to using HU such as bone marrow suppression, concerns over long-term carcinogenic complications, and a 30% non-response rate.

Therefore, it is an object of the invention to provide compositions and methods for treating subjects with one or more mutations in the beta-globin gene (HBB), or an expression control sequence thereof.

It is another object of the invention to provide compositions and methods for treating subjects with sickle cell disease, beta thalassemia, or variants or related diseases or conditions thereof.

It is another object of the invention to provide compositions and methods for reducing one or more symptoms of sickle cell disease, beta thalassemia, or variants or related diseases or conditions thereof.

It is a further object of the invention to provide treatments for sickle cell disease with fewer, or less severe side effects, greater efficacy, greater response rate, or combinations thereof compared to existing therapies such as hydroxyurea.

SUMMARY OF THE INVENTION

Monomethylfumarate induces γ-globin expression and fetal hemoglobin production in human erythroid and retinal pigment epithelial cells. Therefore, methods of treating sickle cell disease (SCD) or complications of SCD include administering an effective amount of one more fumaric acid esters or pharmacologically active salts, derivatives, analogues, or prodrugs thereof to induce or increase expression of fetal hemoglobin (HbF) in a subject in need thereof are disclosed. Another method for treating SCD or complications related to SCD includes administering one or more fumaric acid esters in combination or alternation with hydroxyurea (HU). In one aspect, the subject treated with the combination of fumaric acid ester and HU is typically unresponsive or does not respond well to HU treatment alone. Preferred subjects for treatment with the combination of fumaric acid esters and HU have reduced expression of OCTN1 relative to subjects that respond well to HU treatment alone.

Methods for treating retinopathy due to SCD includes administering one or more fumaric acid esters optionally in combination with HU in an amount effective to increase HbF in retinal pigment epithelial cells.

Examples of suitable fumaric acid esters include, but are not limited to monoethyl fumarate (MEF), monomethyl fumarate (MMF), diethyl fumarate (DEF), and dimethyl fumarate (DMF). In a preferred embodiment, the fumaric acid ester is MMF, DMF, or a combination thereof.

The one or more fumaric acid esters or pharmacologically active salts, derivatives, analogues, or prodrugs thereof are administered to a subject in an effective amount to increase HbF in the subject.

The one or more fumaric acid esters or pharmacologically active salts, derivatives, analogues, or prodrugs thereof can also be administered in an effective amount to increase HbF expression in a subject in need thereof to reduce one or more symptoms of sickle cell disorder in the subject. The sickle cell disorder can be a sickle cell disease such as sickle cell anemia. Typically, the subject has at least one allele of sickle cell hemoglobin (HbS). In some embodiments, the subject has one allele of HbS and one allele of hemoglobin C (HbC), one allele of hemoglobin E (HbE), one allele of β-0 thalassemia, or one allele of β+ thalassemia. In some embodiments, the subject has two alleles of HbS.

The fumaric acid esters or pharmacologically active salts, derivatives, analogues, or prodrugs thereof can be used in combination or alternation with another therapeutic agent to treat SCD or complications of SCD. For example the fumaric acid esters can be combined with HU. The combination of fumaric acid esters with HU can be formulated in a unit does form. Thus, one embodiment is a pharmaceutical composition comprising a fumaric acid ester and HU, optionally including an excipient. An exemplary complication of SCD that can be treated with the disclosed compositions includes but is not limited to retinal complications.

The one or more fumaric acid esters or pharmacologically active salts, derivatives, analogues, or prodrugs thereof can be administered in an effective amount to increase HbF expression in a subject in need thereof to reduce one or more symptoms of a beta-thalassemia in the subject. The beta-thalassemia can be, for example, thalassemia minor, thalassemia intermedia, and thalassemia major.

In some embodiments, the one or more fumaric acid esters or pharmacologically active salts, derivatives, analogues, or prodrugs thereof is administered to a subject in an effective amount to increase HbF expression in the subject in need thereof to compensate for a mutation in the human beta-globin gene. Compensating for a mutation in the human beta globin gene includes inducing expression of HbF.

Methods of increasing HbF expression in hemoglobin synthesizing cells are also disclosed. The methods typically include contacting cells with an effective amount of a fumaric acid ester, or pharmacologically active salt, derivative, analogue, or prodrug thereof to increase HbF expression in the cells. In some embodiments the cells are erythroid precursor cells. Alternatively, the cells are non-erythriod cells such as macrophage, retinal pigment cells, or alveolar epithelial cells.

The one or more fumaric acid esters or pharmacologically active salts, derivatives, analogues, or prodrugs thereof can be in a pharmaceutical composition. The dosage can be between 1 mg/kg to about 50 mg/kg. The dosage can be between 0.1 g and 2.0 g per day. The fumaric acid ester, or pharmacologically active salt, derivative, analogue, or prodrug thereof can be administered as part of a dosage regime. The dosage regime can include dose escalation.

The current labeled dosing of hydroxyurea for sickle cell disease calls for the administration of an initial dose of 15 mg/kg/day in the form of a single dose, with monitoring of the patient's blood count every 2 weeks. If the blood counts are in an acceptable range, the dose may be increased by 5 mg/kg/day every 12 weeks until the MTD of 35 mg/kg/day is reached. Pharmaceutical compositions can contain 1 mg/kg to 50 mg/kg of fumaric acid ester, preferably MMF, in combination with 1 mg/kg to 35 mg/kg of HU.

For example, a dosage regime for treatment of a sickle cell disorder can include administering to a subject with a sickle cell disorder a low dose of a fumaric acid ester, or pharmacologically active salt, derivative, analogue, or prodrug thereof and administering to the subject escalating doses of the fumaric acid ester, or pharmacologically active salt, derivative, analogue, or prodrug thereof until the dose is effective to reduce one or more symptoms of the sickle cell disorder.

Some of the disclosed methods include administering to the subject a second active agent, for example, vitamin supplements, nutritional supplements, anti-anxiety medications, anti-depression medication, anti-coagulants, clotting factors, anti-inflammatories, steroids such as corticosteroids, analgesic, etc. In some embodiments, the compositions are co-administered in combination with one or more additional active agents for treatment of sickle cell disease beta-thalassemia, or a related disorder. Such additional active agents may include, but are not limited to, folic acid, penicillin or another antibiotics, preferably a quinolone or macrolide, antivirals, anti-malarial prophylactics, and analgesics to control pain crises. In some embodiments, the compositions are co-administered with one or more additional agents that increase expression of HbF, for example, hydroxyurea.

Methods of selecting a subject with a mutation in a beta-globin gene for treatment are also disclosed. The methods typically include genotyping the beta-globin gene and expression control sequence thereof in DNA isolated from a biological sample obtained from the subject; determining if the beta-globin gene or expression control sequence includes a mutation; selecting the subject for treatment if the beta-globin gene or expression control sequence includes a mutation; and treating the subject with an effective amount of one or more fumaric acid esters, or pharmacologically active salts, derivatives, analogues, or prodrugs thereof.

Still another method of treatment provides administering fumaric acid esters in combination or alternation with HU to SCD subjects that are unresponsive to HU treatment alone. For example, methylmonofumaric acid ester can be administered to enhance the update of HU in subjects that are typically unresponsive to HU. Unresponsive to HU treatment means that the subject having SCD does not expiring a significant therapeutic effect for treating their SCD from HU treatment. The increase in uptake of HU can also be accompanied by an increase in HfB expression.

BRIEF DESCRIPTION OF THE DRAWINGS

FIG. 7A is a bar graph of γ/γ+β (Fold Change) versus DMF (μM). FIG. 7B is a bar graph of γ/γ+β (fold Change) versus DMF (μM). FIG. 7C is a bar graph of γ/β mRNA level of primary human erythroid progenitors grown in liquid culture treated with DMF, MMF, or HU (μM). The level of γ-globin and β-globin expression was normalized to GAPDH before the γ/β mRNA ratio was calculated. FIGS. 7D(1)-D(4) are line graphs of Relative cell counts versus log fluorescence values for untreated cell (FIG. 7D(1), cells treated with 100 μM HU (FIG. 7D(2), cells treated with 200 μM DMF (Figure D(3), or cells treated with 1000 μM MMF (FIG. 7D(4)). FIG. 7E is a bar graph of FITC Positive Cells (%) in untreated cells (UT, solid bar), cells treated with 200 μM DMF, cells treated with 1000 μM MMF, and cells treated with 100 μM HU. Data were expressed also as the mean concentration of HbF per cell measure.

FIG. 8A shows qPCR analysis of endogenous α-, β- and γ-globin gene expression (Relative Expression) relative to that of hypoxanthine-guanine phosphoribosyltransferase I (internal control) in the human RPE cell line ARPE-19. FIG. 8B is a bar graph showing qPCR used to evaluate γ-globin mRNA expression (Fold Change) in control (UT, untreated) and monomethylfumarate (MMF)-treated cells (1000 μM; 6-24 h). FIG. 8C is a bar graph showing qPCR analysis of endogenous α-, β- and γ-globin gene expression (Relative Globin mRNA/HPRT) relative to that of hypoxanthine-guanine phosphoribosyltransferase I (internal control) in AA (solid bars) and SS (open bars) primary RPE cells. FIG. 8D is a bar graph showing qPCR analysis of γ-globin mRNA expression ((Fold Change) in control (UT, untreated), MMF-treated (100 μM) or HU-treated (100 μM; positive control) AA (solid bars) and SS (open bars) primary RPE cells. FIG. 8E is a bar graph of induction of HbF protein expression (FITC Positive Cells (%)) by the indicated agents evaluated in AA (solid bars) and SS (open bars) primary RPE cells by FACS using the FITC-conjugated anti-γ-globin antibody and, the number of FITC-positive cells normalized to isotype controls expressed in graphical format. HbF protein expression was confirmed by Western blot. MMF (1 mM final concentration) or phosphate buffered saline (PBS; 0.01 M pH 7.4) was injected intravitreally into the eyes of live AA and SS mince (n=6); 24 h later, γ-globin mRNA expression in RPE/eyecup and HbF protein in intact retina was evaluated by qPCR (FIG. 8F).

DETAILED DESCRIPTION OF THE INVENTION

I. Definitions

Figure 1:
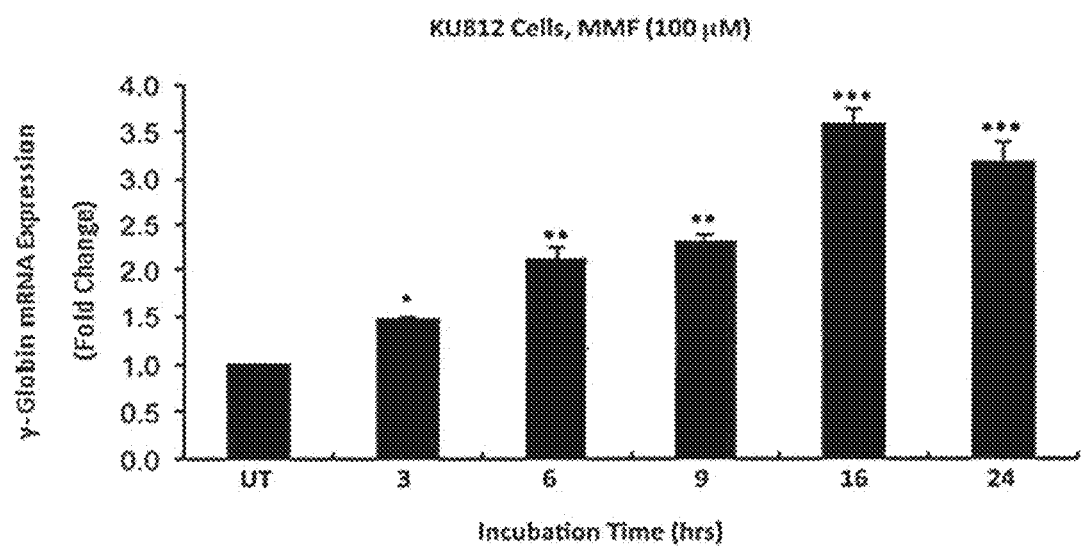
FIG. 1 is a bar graph showing the change in γ-globin mRNA expression (fold change compared to untreated control ("UT")) in KU812 cells over time (hours) following treatment with 100 µM monomethylfumarate (MMF) treatment. Data are represented as means±standard error of the mean (SEM); *$P<0.05$, $P<0.01$ and *$P<0.001$.

The term "expression control sequence" refers to a nucleic acid sequence that controls and regulates the transcription and/or translation of another nucleic acid sequence. Control sequences that are suitable for prokaryotes, for example, include a promoter, optionally an operator sequence, a ribosome binding site, and the like. Eukaryotic cells are known to utilize promoters, polyadenylation signals, and enhancers.

The term "gene" refers to a DNA sequence that encodes through its template or messenger RNA a sequence of amino acids characteristic of a specific peptide, polypeptide, or protein. The term "gene" also refers to a DNA sequence that encodes an RNA product. The term gene as used herein with reference to genomic DNA includes intervening, non-coding regions as well as regulatory regions and can include 5' and 3' ends.

As generally used herein "pharmaceutically acceptable" refers to those compounds, materials, compositions, and/or dosage forms which are, within the scope of sound medical judgment, suitable for use in contract with the tissues, organs, and/or bodily fluids of human beings and animals without excessive toxicity, irritation, allergic response, or other problems or complications commensurate with a reasonable benefit/risk ratio.

The terms "subject," "individual," and "patient" refer to any individual who is the target of treatment using the disclosed compositions. The subject can be a vertebrate, for example, a mammal. Thus, the subject can be a human. The subjects can be symptomatic or asymptomatic. The term does not denote a particular age or sex. Thus, adult and newborn subjects, whether male or female, are intended to be covered. A subject can include a control subject or a test subject. The test subject can be a subject afflicted with a genetic mutation in the beta-globin gene or an expression control sequence thereof, or a subject with a sickle cell disorder, a globinopathy, or a beta-thalassemia.

As used herein, the term "treating" includes alleviating the symptoms associated with a specific disorder or condition and/or preventing or eliminating said symptoms.

The term "alkyl" refers to the radical of saturated aliphatic groups, including straight-chain alkyl groups, branched-chain alkyl groups, cycloalkyl (alicyclic) groups, alkyl-substituted cycloalkyl groups, and cycloalkyl-substituted alkyl groups.

In preferred embodiments, a straight chain or branched chain alkyl has 30 or fewer carbon atoms in its backbone (e.g., C1-C30 for straight chains, C3-C30 for branched chains), preferably 20 or fewer, more preferably 15 or fewer, most preferably 10 or fewer. Likewise, preferred cycloalkyls have from 3-10 carbon atoms in their ring structure, and more preferably have 5, 6, or 7 carbons in the ring structure. The term "alkyl" (or "lower alkyl") as used throughout the specification, examples, and claims is intended to include both "unsubstituted alkyls" and "substituted alkyls", the latter of which refers to alkyl moieties having one or more substituents replacing a hydrogen on one or more carbons of the hydrocarbon backbone. Such substituents include, but are not limited to, halogen, hydroxyl, carbonyl (such as a carboxyl, alkoxycarbonyl, formyl, or an acyl), thiocarbonyl (such as a thioester, a thioacetate, or a thioformate), alkoxyl, phosphoryl, phosphate, phosphonate, phosphinate, amino, amido, amidine, imine, cyano, nitro, azido, sulfhydryl, alkylthio, sulfate, sulfonate, sulfamoyl, ulfonamide, sulfonyl, heterocyclyl, aralkyl, or an aromatic or heteroaromatic moiety.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths. Throughout the application, preferred alkyl groups are lower alkyls. In preferred embodiments, a substituent designated herein as alkyl is a lower alkyl.

It will be understood by those skilled in the art that the moieties substituted on the hydrocarbon chain can themselves be substituted, if appropriate. For instance, the substituents of a substituted alkyl may include halogen, ulfonam, nitro, thiols, amino, azido, imino, amido, phosphoryl (including phosphonate and phosphinate), sulfonyl (including sulfate, ulfonamide, sulfamoyl and sulfonate), and silyl groups, as well as ethers, alkylthois, carbonyls (including ketones, aldehydes, carboxylates, and esters), —CF3, —CN and the like. Cycloalkyls can be substituted in the same manner.

"Aryl", as used herein, refers to C5-C10-membered aromatic, heterocyclic, fused aromatic, fused heterocyclic, biaromatic, or bihetereocyclic ring systems. Broadly defined, "aryl", as used herein, includes 5-, 6-, 7-, 8-, 9-, and 10-membered single-ring aromatic groups that may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycles" or "heteroaromatics". The aromatic ring can be substituted at one or more ring positions with one or more substituents including, but not limited to, halogen azide, alkyl, aralkyl, alkenyl, alkynyl, cycloalkyl, hydroxyl, alkoxyl, amino (or quaternized amino), nitro, sulfhydryl, imino, amido, phosphonate, phosphinate, carbonyl, carboxyl, silyl, ether, alkylthio, sulfonyl, ulfonamide, ketone, aldehyde, ester, heterocyclyl, aromatic or heteroaromatic moieties, —CF3, —CN; and combinations thereof.

The term "aryl" also includes polycyclic ring systems having two or more cyclic rings in which two or more carbons are common to two adjoining rings (i.e., "fused rings") wherein at least one of the rings is aromatic, e.g., the other cyclic ring or rings can be cycloalkyls, cycloalkenyls, cycloalkynyls, aryls and/or heterocycles. Examples of heterocyclic rings include, but are not limited to, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH carbazolyl, carbolinyl, chromanyl, chromenyl, cinnolinyl, decahydroquinolinyl, 2H,6H-1,5,2-dithiazinyl, dihydrofuro[2,3-b]tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylendedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl and xanthenyl. One or more of the rings can be substituted as defined above for "aryl".

II. Methods of Treating Sickle Cell Disease, Beta-Thalassemias, and Related Disorders

A. Treatment of SCD with Fumaric Acid Esters

Methods of increasing expression of HbF in cells by contacting the cells, for example erythroid and RPE cells, with an effective amount of a fumaric acid ester, or pharmacologically active salt, derivative, analogue or prodrug thereof are disclosed. The methods can be used to compensate for a mutation in the human beta-globin gene in cells that have one or more mutations in the beta-globin gene or an expression control sequence thereof, for example mutations that result in the expression of the Hb S from of hemaglobin. Compensating for the mutation includes but is not limited to increasing the amount of HbF and reducing the amount of Hb S in the subject compared to untreated subjects. The methods can be used for treating sickle cell disease, for example sickle cell anemia, and other hemoglobinopathies or thalassemias as well as complications related to SCD, for example retinopathy.

B. Treatment of Fumaric Acid Esters in Combination or Alternation with HU.

Methods for treating SCD or complications thereof include administering fumaric acid esters in combination or alternation with HU in amounts effective to induce or increase expression of HbF and increase expression of OCTN1 in erythroid and retinal cells. It has been discovered that MMF induce the expression of SLC22A4 (aka OCTN10, a transporter shown recently to transport HU (Walker A L et al. *Exp. Hematol.* 2011; 39(4):446-56). The expression of OCTN1 and its induction by MMF is evident in retinal and erythroid cells. MMF can increase the entry of HU into erythroid progenitor cells and facilitate the action of HU on fetal hemoglobin production. In some embodiments, MMF can reduce the dosing of HU in SCD patients without compromising its therapeutic efficacy, and reduce the toxic side effects associated with HU therapy.

Subjects with SCD that are unresponsive to HU treatment can be treated by administering a fumaric acid ester in combination or alternation with HU. While MMF adjuvant therapy along with HU would certainly benefit SCD patients who respond to HU, it also has potential to work on those who do not respond to HU. In one embodiment, the "non-responders" express lower levels of OCTN1 than "responders." The decreased expression of the transporter would result in decreased entry of HU into its target cells (erythroid progenitors) and thus decrease its pharmacological effect. Since MMF induces OCTN1, adjuvant therapy is likely to enhance the entry of HU in 'non-responders" and thereby make the patients to become responsive to HU therapy. This is in addition to the effect of MMF itself in increasing fetal hemoglobin production.

Fumaric acid esters have been used for greater than 50 years in the treatment of psoriasis, and more recently multiple sclerosis. It is believed that the beneficial effects of fumaric acid esters in the treatment of these pathologic conditions are due to their potent anti-inflammatory and anti-oxidant effects. It has been discovered that in addition to the known, robust anti-inflammatory and anti-oxidant properties, these compounds also induce production of fetal hemoglobin (HbF) in cells. Reactivation of HbF, which is typically absent or expressed only at low levels in humans over six months of age, is considered a viable approach for treating children and adults with sickle cell disease, and other hemoglobinopathies and thalassemias. The methods disclosed herein typically include administering a fumaric acid ester, or pharmacologically active salt, derivative, analogue or prodrug thereof to a subject in need thereof to increase expression of HbF in the subject, to increase expression of OCTN1, or both.

C. Diseases to be Treated

The disclosed compositions can be used to treat subjects with one or more mutations in the beta-globin gene (HBB gene). Mutations in the beta globin gene can cause sickle cell disease, beta thalassemia, or related diseases or conditions thereof. As discussed in more detail below, mutations in the beta-globin gene can be identified before or after manifestations of a disease's clinical symptoms. The compositions can be administered to a subject with one or more mutations in the beta-globin gene before or after the onset of clinical symptoms. Therefore, in some embodiments, the compositions are administered to a subject that has been diagnosed with one or more mutations in the beta-globin gene, but does not yet exhibit clinical symptoms. In some embodiments, the compositions are administered to a subject that is exhibiting one ore more symptoms of a disease, condition, or syndrome associated with, or caused by one or more mutations in the beta-globin gene.

1. Sickle Cell Disease

Sickle cell disease (SCD) typically arises from a mutation substituting thymine for adenine in the sixth codon of the beta-chain gene of hemoglobin (i.e., GAG to GTG of the HBB gene). This mutation causes glutamate to valine substitution in position 6 of the Hb beta chain. The resulting Hb, referred to as HbS, has the physical properties of forming polymers under deoxy conditions. SCD is typically an autosomal recessive disorder. Therefore, in some embodiments, the disclosed compositions and methods are used to treated a subject homozygous for an autosomal recessive mutation in beta-chain gene of hemoglobin (i.e., homozygous for sickle cell hemoglobin (HbS)). Also referred to as HbSS disease or sickle cell anemia (the most common form), subjects homozygote for the S globin typically exhibit a severe or moderately sever phenotype and have the shortest survival of the hemaglobinopathies.

Sickle cell trait or the carrier state is the heterozygous form characterized by the presence of around 40% HbS, absence of anemia, inability to concentrate urine (isosthenuria), and hematuria. Under conditions leading to hypoxia, it may become a pathologic risk factor. Accordingly, in some embodiments, the disclosed compositions and methods are used to treat a subject heterozygous for an autosomal recessive mutation in the beta-chain gene of hemoglobin (i.e., heterozygous for HbS).

2. Beta-Thalassemia

Beta-thalassemias (β-thalassemias) are a group of inherited blood disorders caused by a variety of mutational mechanisms that result in a reduction or absence of synthesis of β-globin and leading to accumulation of aggregates of upaired, insoluble α-chains that cause ineffective erythropoiesis, accelerated red cell destruction, and severe anemia. Subjects with beta-thalassemia exhibit variable phenotypes ranging from severe anemia to clinically asymptomatic individuals. The genetic mutations present in β thalassemias are diverse, and can be caused by a number of different mutations. The mutations can involve a single base substitution or deletions or inserts within, near or upstream of the β globin gene. For example, mutations occur in the promoter regions preceding the beta-globin genes or cause production of abnormal splice variants.

Examples of thalassemias include thalassemia minor, thalassemia intermedia, and thalassemia major.

Thalassemia minor refers to thalassemia where only one of beta-globin alleles bears a mutation. Individuals typically suffer from microcytic anemia. Detection usually involves lower than normal MCV value (<80 fL) plus an increase in fraction of Hemoglobin A2 (>3.5%) and a decrease in fraction of Hemoglobin A (<97.5%). Genotypes can be β+/β or β-0/β.

Thalassemia intermedia refers to a thalassemia intermediate between the major and minor forms. Affected individuals can often manage a normal life but may need occasional transfusions, e.g., at times of illness or pregnancy, depending on the severity of their anemia. Genotypes can be β+/β+ or β-0/β.

Thalassemia major refers to a thalassemia where both beta-globin alleles have thalassemia mutations. This is a severe microcytic, hypochromic anemia. If left untreated, it causes anemia, splenomegaly, and severe bone deformities and typically leads to death before age 20. Treatment consists of periodic blood transfusion-caused iron overload. Cure is possible by bone marrow transplantation. Cooley's anemia is named after Thomas Benton Cooley. Genotypes include β+/β-0 or β-0/β-0 or β+/β+.

3. Sickle Cell Related Disorders

Although carriers of sickle cell trait do not suffer from SCD, individuals with one copy of HbS and one copy of a gene that codes for another abnormal variant of hemoglobin, such as HbC or Hb beta-thalassemia, have a less severe form of the disease. For example, another specific defect in beta-globin causes another structural variant, hemoglobin C (HbC). Hemoglobin C (abbreviated as Hb C or HbC) is an abnormal hemoglobin in which substitution of a glutamic acid residue with a lysine residue at the $6^{th}$ position of the β-globin chain has occurred. A subject that is a double heterozygote for HbS and HbC (HbSC disease) is typically characterized by symptoms of moderate clinical severity.

Another common structural variant of beta-globin is hemoglobin E or hemoglobin E (HbE). HbE is an abnormal hemoglobin in which substitution of a glutamic acid residue with a lysine residue at the $26^{th}$ position of the β-globin chain has occurred. A subject that is a double heterozygote for HbS and HbE has HbS/HbE syndrome, which usually causes a phenotype similar to HbS/b+ thalassemia, discussed below.

Some mutations in the beta-globin gene can cause other structural variations of hemoglobin or can cause a deficiency in the amount of β-globin being produced. These types of mutations are referred to as beta-thalassemia mutations.

The absence of beta-globin is referred to as beta-zero (β-0) thalassemia. A subject that is a double heterozygote for HbS and β-0 thalassemia (i.e., HbS/β-0 thalassemia) can suffer symptoms clinically indistinguishable from sickle cell anemia.

A reduced amount of beta-globin is referred to as β-plus (β+) thalassemia. A subject that is a double heterozygote for HbS and β+ thalassemia (i.e., HbS/β+ thalassemia) can have mild-to-moderate severity of clinical symptoms with variability among different ethnicities.

Rare combinations of HbS with other abnormal hemoglobins include HbD Los Angeles, G-Philadelphia, HbO Arab, and others.

Therefore, in some embodiments, the disclosed compositions and methods are used to treating a subject with an HbS/β-0 genotype, an HbS/β+ genotype, an HBSC genotype, an HbS/HbE genotype, an HbD Los Angeles genotype, a G-Philadelphia genotype, or an abHbO Arab genotype.

As discussed above, retinopathy due to SCD can also be treated by administering an effective amount of a fumaric acid ester, for example MMF, optionally in combination or alternation with HU in amounts effective to induce expression of HbF in retinal cells, for example in RPE cells. Sickle retinopathy occurs when the retinal blood vessels get occluded by sickle red blood cells and the retina becomes ischemic, angiogenic factors are made in retina. In sickle cell disease, this occurs mostly in the peripheral retina, which does not obscure vision at first. Eventually, the entire peripheral retina of the sickle cell patient becomes occluded and many neovascular formations occur. Administration of one or more fumaric acid esters optionally in combination with HU can reduce or inhibit the formation of occlusions in the peripheral retina of a sickle cell patient.

4. Non-erythroid Cell Related Disorders

Although red blood cells are the primary producers of hemoglobin, reports indicate that other, non-hematopoietic cells, including, but not limited to, macrophage, retinal pigment cells, and alveolar epithelial cells such as alveolar type II (ATII) cells and Clara cells which are the primary producers of pulmonary surfactant, also synthesize hemoglobin (Newton, et al., *J. Biol. Chem.*, 281(9)5668-5676 (2006), Tezel et al., *Invest. Ophthalmol. Vis. Sci.*, 50(4): 1911-9 (2009), Liu, et al., *Proc. Natl. Acad. Sci. USA*, 96(12)6643-6647 (1999)). These findings are consistent with the conclusion that the expression of hemoglobin by non-erythroid cells at interlaces where oxygen-carbon dioxide diffusion occurs may be an adaptive mechanism to facilitate oxygen transport (Tezel, et al., *Invest. Ophthalmol. Vis. Sci.*, 50(4):1911-9 (2009).

Therefore, in some embodiments, the compositions disclosed herein are used to increase HbF expression, in non-erythroid cells including, but not limited to, macrophage, retinal pigment cells, and alveolar epithelial cells such as alveolar type II (ATII) cells and Clara cells. In some embodiments, the compositions disclosed herein are used to increase HbF expression in non-erythroid cells at interfaces where oxygen-carbon dioxide diffusion occurs, including, but not limited to the eyes and lungs. In some embodiments, the compositions are used to induce, increase, or enhance hemoglobin synthesis retinal pigment cells in an effective amount to prevent, reduce, or alleviate one or more symptoms of age-related macular degeneration or diabetic retinopathy.

D. Symptoms of Sickle Cell Disease, Beta-thalassemias, and Related Disorders

In some embodiments, the compositions disclosed, herein are administered to a subject in an effective amount to treatment one or more symptoms of sickle cell disease, a beta-thalassemia, or a related disorder.

Beta-thalassemia can include symptoms such as anemia, fatigue and weakness, pale skin or jaundice (yellowing of the skin), protruding abdomen with enlarged spleen and liver, dark urine, abnormal facial bones and poor growth, and poor appetite.

In subjects with sickle cell disease, or related disorder, physiological changes in RBCs can result in a disease with the following signs: (1) hemolytic anemia; (2) vaso-occlusive crisis; and (3) multiple organ damage from microinfarcts, including heart, skeleton, spleen, and central nervous system.

Chronic Hemolytic Anemia

SCD is a form of hemolytic anemia, with red cell survival of around 1-20 days. Approximately one third of the hemolysis occurs intravascularly, releasing free hemoglobin (plasma free hemoglobin [PFH]) and arginase into plasma. PFH has been associated with endothelial injury including scavenging nitric oxide (NO), proinflammatory stress, and coagulopathy, resulting in vasomotor instability and proliferative vasculopathy. A hallmark of this proliferative vasculopathy is the development of pulmonary hypertension in adulthood.

Vaso-Occlusive Crisis

Vaso-occlusive crisis occurs when the circulation of blood vessels is obstructed by sickled red blood cells, causing ischemic injuries. The most common complaint is of pain, and recurrent episodes may cause irreversible organ damage. One of the most severe forms is the acute chest syndrome which occurs as a result of infarction of the lung parenchyma. Vaso-occlusive crisis can be accompanied by a pain crisis which can occur suddenly and last several hours to several days.

The pain can affect any body part. It often involves the abdomen, bones, joints, and soft tissue, and it may present as dactylitis (bilateral painful and swollen hands and/or feet in children), acute joint necrosis or avascular necrosis, or acute abdomen. With repeated episodes in the spleen, infarctions and autosplenectomy predisposing to life-threatening infection are usual. The liver also may infarct and progress to failure with time. Papillary necrosis is a common renal manifestation of vaso-occlusion, leading to isosthenuria (i.e., inability to concentrate urine).

Severe deep pain is present in the extremities, involving long bones. Abdominal pain can be severe, resembling acute abdomen; it may result from referred pain from other sites or intra-abdominal solid organ or soft tissue infarction. Reactive ileus leads to intestinal distention and pain.

Bone pain and abdominal pain may be present. The face also may be involved. Pain may be accompanied by fever, malaise, and leukocytosis.

Skeletal Manifestations

Skeletal manifestations include, but are not limited to, infarction of bone and bone marrow, compensatory bone marrow hyperplasia, secondary osteomyelitis, secondary growth defects, intravascular thrombosis, osteonecrosis (avascular necrosis/aseptic necrosis), degenerative bone and joint destruction, osteolysis (in acute infarction), Articular disintegration, myelosclerosis, periosteal reaction (unusual in the adult), H vertebrae (steplike endplate depression also known as the Reynold sign or codfish vertebrae), Dystrophic medullary calcification, bone-within-bone appearance, decreased density of the skull, decreased thickness of outer table of skull due to widening of diploe, hair on-end striations of the calvaria, osteoporosis sometimes leading to biconcave vertebrae, coarsening of trabeculae in long and flat bones, and pathologic fractures, bone shortening (premature epiphyseal fusion), epiphyseal deformity with cupped metaphysis, peg-in-hold defect of distal femur, and decreased height of vertebrae (short stature and kyphoscoliosis).

Renal Manifestations

Renal manifestations include, but are not limited to, various functional abnormalities such as hematuria, proximal tubule dysfunction, impaired potassium excretion, and hyperkalemia; and gross anatomic alterations, for example, hypertrophied kidneys, with a characteristic smooth, capsular surface.

Splenic Manifestations

Splenic manifestations include, but are not limited to, enlargement, including rapid and/or painful enlargement known as splenic sequestration crisis, infarction, low pH and low oxygen tension in the sinusoids and splenic cords, functional impairment, autosplenectomy (fibrosis and shrinking of the spleen in advanced cases), immune deficiency and increased risk of sepsis.

Other Common Symptoms

Lower serum immunoglobulin M (IgM) levels, impaired opsonization, and sluggish alternative complement pathway activation, increase susceptibility to infection pneumonia, bronchitis, cholecystitis, pyelonephritis, cystitis, osteomyelitis, meningitis, and sepsis and other challenges from infectious agents including, but not limited to, *Mycoplasma pneumoniae, Salmonella typimurium, Staphylococcus aureus,* and *Escherichia coli*; growth delays or maturation delays during puberty in adolescents, hand-foot syndrome, acute chest syndrome, stroke, hemiparesis, hemosiderin deposition in the myocardium, dilation of both ventricles and the left atrium, cholelithiasis, paraobital facial infarction, retinal vascular changes, proliferative retinitis, loss of vision, leg ulcers, priapism, avascular necrosis, and pulmonary hypertension.

III. Compositions for Use in Treating Sickle Cell Disease, Beta-thalassemia, or Related Disorders A. Active Agents 1. Fumaric Acid Esters The methods disclosed herein typically include administering a subject in need thereof one or more fumaric acid esters or pharmacologically active salts, derivatives, analogues or prodrugs thereof. In preferred embodiments, the one or more fumaric acid esters, pharmacologically active salts, derivatives, analogues, or prodrugs thereof are part of pharmaceutical compositions which can include a pharmaceutically acceptable carrier. Fumaric acid esters (FAE) are agents derived from the unsaturated dicarbonic acid, fumaric acid. Fumaric acid is a white crystalline powder with a characteristic acidic taste that is commonly used as a food additive and flavoring agent in cakes and sweets. Fumaric acid is poorly absorbed and believed to pass through the body without causing any effects. However, esters of fumaric acid (FAEs) are potent chemicals and recognized for their ability to treat clinical symptoms of psoriasis and multiple sclerosis.

In one embodiment, the fumaric acid ester has the following formula:

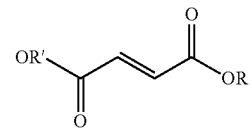

wherein R and R' are independently selected from the group consisting of hydrogen or substituted or unsubstituted alkyl, heteroalkyl, cycloalkyl, heterocycloalkyl, alkenyl, heteroalkenyl, cycloalkenyl, heterocycloalkenyl, aryl, and heteroaxyl, with the provision that R and R' are not both hydrogen.

In some embodiments, one or both of R and R' are lower alkyl (e.g., $C_1$-$C_4$), such as substituted or unsubstituted methyl or ethyl. Exemplary FAEs include, but are not limited to, monoethyl fumarate (MEF), monomethyl fumarate (MMF), diethyl, fumarate (DEF), dimethyl fumarate (DMF), as well as pharmacologically active salts, derivatives, analogues, or prodrugs thereof.

Relationships between the physicochemical properties of the fumaric acid esters, including their presystemic metabolism and intestinal absorption, are known in the art. See, for example, Werdenberg, et al., *Biopharm. Drug Dispos.,* 24(6):259-73 (2003), which reports that the intestinal permeability of the monoesters methyl hydrogen fumarate, ethyl hydrogen fumarate, n-propylhydrogen fumarate and n-pentyl hydrogen fumarate increase with an increase in their lipophilicity, however, their presystemic metabolism rates likewise increase with increasing ester chain length. Therefore, it is believed that for fumarates, an increase in intestinal permeability of the more lipophilic derivatives is counterbalanced by an increase in first-pass extraction.

Additional studies on characterizing the intestinal absorption of fumaric acid esters indicate that uncharged diester dimethylfumarate displays a high presystemic metabolic liability and high permeability in an in vitro small intestinal cell model (Werdenberg, et al., *Biopharm. Drug Dispos.*, 24(6):259-73 (2003)). Results also show complete metabolism of DFM in the intestinal tissue.

DMF is rapidly hydrolysed by esterases to the metabolite MMF. Accordingly, in a preferred embodiment the fumaric acid ester is DMF, MMF, or a combination thereof. In some embodiments, the compositions also includes Monoethyl fumarate.

Formulations including dimethyl fumarate and ethyl hydrogen fumarate have been used in the treatment of psoriasis for many years. One family of such formulations are marketed under the tradename FUMADERM. FUMADERM is in the form of tablets intended for oral use and it is available in two different dosage strengths (FUMADERM Initial and FUMADERM):

TABLE 1

Components and Quantitative Composition of FUMADERM
(U.S. Patent Application 2008/0004344)

| | Fumaderm ® Initial | Fumaderm ® |
|---|---|---|
| Dimethylfumarate | 30 mg | 120 mg |
| Ethylhydrogenfumarate, calcium salt | 67 mg | 87 mg |
| Ethylhydrogenfumarate, Magnesium salt | 5 mg | 5 mg |
| Etylhydrogenfumarate, Zinc salt | 3 mg | 3 mg |

For the treatment of psoriasis, the two strengths are typically applied in an individually based dose regimen starting with FUMADERM Initial in an escalating dose, and then after e.g., three weeks of treatment switching to FUMADERM. Both FUMADERM Initial and FUMADERM are enteric coated tablets. In some embodiments, the composition used in the methods disclosed herein includes FUMADERM Initial, FUMADERM, or a combination thereof.

Another marketed composition is FUMARAAT 120 which contains 120 mg of dimethylfumarate and 95 mg of calcium monoethylfumarate (TioFarma, Oud-Beijerland, Netherlands). In the publication (Litjens et al. *Br. J. Clin. Pharmacol.* 2004, vol. 58:4, pp. 429-432), the pharmacokinetic profile of FUMARAAT 120 was reported in healthy subjects. The results show that a single oral dose of FUMARAAT 120 is followed by a rise in serum monomethylfumarate concentration and only negligible concentrations of dimethylfumarate and fumaric acid is observed. The results indicate that dimethylfumarate is rapidly hydrolyzed to monomethylfumarate in an alkaline environment, but according to the authors not in an acid environment. As the composition is enteric coated, it is believed that the uptake of fumarate takes place mainly in the small intestine. It is believed that dimethylfumarate is either hydrolysed to the monoester before uptake due to an alkaline environment or it is rapidly converted to monoester by esterases in the circulation. In some embodiments, the composition used in the methods disclosed herein includes FUMARAAT 120.

The study also shows that time to peak concentration ($T_{max}$) and peak concentration ($C_{max}$) are subject to food effect, i.e., $T_{max}$ is prolonged (mean for fasted conditions is 182 min, whereas for fed conditions mean is 361 min) [lag time is 90 min for fasted and 300 min for fed] and $C_{max}$ is decreased (fasted: 0.84 mg/l, fed: 0.48 mg/l) by concomitant food-intake.

Another study, in healthy subjects with two tablets of FUMADERM, revealed $C_{max}$ values (determined as mono-ethyl- or monomethylfumarate) in a range from 1.0 to 2.4 µg/ml and a $T_{max}$ in a range of from 4.8 to 6.0 hours. (Reddingius W. G. Bioanalysis and Pharmacokinetics of Fumarates in Humans. Dissertation ETH Zurich No. 12199 (1997)).

U.S. Published Application 2012/0165404, which is specifically incorporated by reference herein in its entirety, describes compositions referred to as BG00012, an orally available formulation of dimethyl fumarate (DMF) which is in clinical development for treatment of relapsing-remitting multiple sclerosis (RRMS). U.S. Published Application 2012/0165404, describes that some embodiments in which dimethyl fumarate is administered to a patient the DMF is formulated in capsules containing enteric coated microtablets referred to "BG-12" or "BG00012." The coating of the tablets is composed of different layers. The first layer is a methacrylic acid-methyl methacrylate copolymer/isopropyl alcohol solution which isolates the tablet cores from potential hydrolysis from the next applied water suspensions. Enteric coating of the tablet is then conferred by an aqueous methacrylic acid-ethyl acrylate copolymer suspension. In some embodiments, the composition used in the methods disclosed herein includes BG00012. The complete components and quantitative composition of the capsules are given in Table 2.

TABLE 2

Components and Quantitative Composition of BG00012,
(U.S. Patent Application No. 2012/0165404)

| Ingredients | Amount/capsule | Function |
|---|---|---|
| Core Microtablets Active ingredients: | | |
| Dimethyl Fumarate* | 120.00 mg | active ingredient |
| Excipients: | | |
| Croscarmellose sodium | 15.00 mg | disintegrant |
| Microcrystalline Cellulose | 131.60 mg | filler |
| Magnesium stearate | 5.00 mg | lubricant |
| Talcum | 19.80 mg | glidant |
| Silica colloidal anhydrous | 2.60 mg | glidant |
| Mass core microtablets | 294.00 mg | |
| Coating Microtablets Excipients: | | |
| Triethyl Citrate** | 7.60 mg | plasticizer |
| Methacrylic Acid-Methyl Methacrylate Copolymer (1:1) as | 5.50 mg | film coating agent |
| Methacrylic Acid-Methyl Methacrylate Copolymer (1:1) solution 12.5%** | (44.00 mg) | |
| Simeticone (corresponding to Simeticone Ph Eur) as | 0.17 mg | anti-foam agent |
| Simeticone Emulsion USP** | (0.53 mg) | |
| Talcum micronised** | 13.74 mg | lubricant |
| Methacrylic acid - Ethyl Acrylate Copolymer (1:1) as | 33.00 mg | film coating agent |
| Methacrylic acid - Ethyl Acrylate Copolymer (1:1) dispersion 30% ** | (110.00 mg) | |
| Mass enteric coated microtablets | 354.01 mg | |
| Mass of gelatin capsule | 96.00 mg | |
| Mass of filled capsule | 450.01 mg | |

In some embodiments, the fumaric acid ester is a prodrug of a fumaric acid ester. Preliminary results from a Phase 1 clinical trial in healthy adults designed to assess the pharmacokinetics (PK), safety and tolerability of single doses of four different oral formulations of a fumaric acid ester compound that is a prodrug of monomethyl fumarate (MMF) referred to as XP23829 were favorable (XenoPort Press Release, "XenoPort Reports Favorable Metabolism and Pharmacokinetics of XP23829, a Novel Fumaric Acid Ester, in Phase 1 Trial" (2012)). XP23829 is being developed for the potential treatment of relapsing-remitting multiple sclerosis (RRMS) and/or psoriasis. The trial showed that administration of XP223829 resulted in the expected levels of MMF in the blood. The four formulations produced different PK profiles of MMF, including on formulation that could potentially be dosed two or three times a day and at least one formulation that may be suitable for once-a-day dosing. XP23829 was generally well-tolerated in the trial. U.S. Patent Application Nos. 2012/0157523, 2012/0095003, and 2010/00048651, each of which is incorporated by reference in its entirety, discuss prodrugs of methyl hydrogen fumarate, pharmaceutical compositions thereof and methods of use. In some embodiments, the fumaric acid ester is a fumaric acid ester prodrug such as XP23829, or pharmacologically active salt, an analogue or derivative thereof.

Other suitable fumaric acid ester compounds, pharmaceutical compositions, and formulations suitable for use in the disclosed methods are known in the art. See for example, U.S. Pat. Nos. 6,509,376, 6,436,992, 6,277,82, 6,355,67, 6,509,376, 4,959,389, and U.S. Patent Application No. 2008/0004344, each of which is incorporated by reference in its entirety. U.S. Pat. Nos. 6,509,376 and 6,436,992 discuss formulations containing DMF and/or MMF. U.S. Pat. Nos. 6,277,882 and 6,355,676 describe the use of alkyl hydrogen fumarates and certain fumaric acid mono alkyl ester salts, respectively, for preparing micro tablets for treating psoriasis, psoriatic arthritis, neurodermatitis and enteritis regionalis. U.S. Pat. No. 6,509,376 describes that use of certain dialkyl fumarates pharmaceutical preparations for use in transplantation medicine or the therapy of autoimmune diseases in the form of micro tablets or pellets, U.S. Pat. No. 4,959,389, which describes compositions containing different salts of fumaric acid monoalkyl ester alone or in combination with dialkyl fumarate, and U.S. Patent Application No. 2008/0004344, which describes salts of fumaric acid monoalkylesters and their pharmaceutical use. The Case report "Treatment of disseminated granuloma annulare with fumaric acid esters" from *BMC Dermatology, vol.* 2, no. 5, 2002, relates to treatment with fumaric acid esters.

2. Co-Administration

The compositions disclosed herein can optionally include, or be co-administered with one or more additional active agents. Co-administration can include the simultaneous and/ or sequential administration of the one or more additional active agents and one or more fumaric acid ester, or pharmacologically active salt, derivative, analogue, or prodrug thereof. The one or more additional active agents and the fumaric acid ester, or pharmacologically active salt, derivative, analogue, or prodrug thereof can be included in the same or different pharmaceutical formulation. The one or more additional active agents and the fumaric acid ester, or pharmacologically active salt, derivative, analogue, or prodrug thereof can achieve the same or different clinical benefit. An appropriate time course for sequential administration may be chose by the physician, according to such factors as the nature of a patient's illness, and the patient's condition. In certain embodiments, sequential administration includes the co-administration of one or more additional active agents and the nanoparticle gene carriers within a period of one week, 72 hours, 48 hours, 24 hours, or 12 hours.

The additional active agent can be chosen by the user based on the condition or disease to be treated. Example of additional active agents include, but are not limited to, vitamin supplements, nutritional supplements, anti-anxiety medication, anti-depression medication, anti-coagulants, clotting factors, anti-inflammatories, steroids such a corticosteroids, analgesic, etc.

In some embodiments, the compositions disclosed herein are co-administered in combination with one or more additional active agents for treatment of sickle cell disease, beta-thalassemia, or a related disorder. Such additional active agents may include, but are not limited to, folic acid, penicillin or another antibiotics, preferably a quinolone or macrolide, antivirals, anti-malarial prophylactics, and analgesics to control pain crises.

In some embodiments, the compositions are co-administered with one or more additional agents that increase expression of HbF, for example, hydroxyurea.

In some embodiments, the compositions are co-administered with one or more additional treatment protocols, for example, transfusion therapy, stem cell therapy, gene therapy, bone marrow transplants, dialysis or kidney transplant for kidney disease, gallbladder removal in people with gallstone disease, hip replacement for avascular necrosis of the hip, surgery for eye problems, and would care for leg ulcers.

B. Effective Amounts

In some embodiments, the compositions are administered in an amount effective to induce a pharmacological, physiological, or molecular effect compared to a control that is not administered the composition. In some embodiments, a fumaric acid ester, or pharmacologically active salt, derivative, analogue, or prodrug thereof is administered to a subject in need thereof to increase expression of HbF in the subject. For example, HbF expression can be increased in an amount effective to compensate for, or reduce the effects of a mutation in the HBB gene. In some embodiments, the fumaric acid ester, or pharmacologically active salt, derivative, analogue, or prodrug thereof is administered in an effective amount to reduce the sickling of red blood cells in a patient relative to a control.

In some embodiments, the fumaric acid ester, or pharmacologically active salt, derivative, analogue, or prodrug thereof is provided in an effective amount to prevent, reduce or alleviate one or more symptoms of a disease or disorder to be treated. For example, the compositions disclosed herein can be administered to a subject in need thereof in an effective amount to reduce or alleviate one or more symptoms of sickle cell disease, a beta-thalassemia, or a sickle cell related disorder, including, but not limited to, the symptoms discussed above.

Suitable controls are known in the art and can be determined based on the disease to be treated. Suitable controls include, but are not limited to a subject, or subjects without sickle cell disease, a beta-thalassemia, or a sickle cell related disorder; or a condition or status of a subject with the disease or disorder prior to initiation of the treatment. For example, in some embodiments, treatment of a subject with a fumaric acid ester, or pharmacologically active salt, derivative, analogue, or prodrug thereof improves one or more pharmacological, physiological, or molecular effects; reduces or alleviates one or more symptoms of the disease or disorder to be treated; or a combination thereof compared to a subject or subjects without the disease or disorder to be treated. In some embodiments, treatment of a subject with a fumaric acid ester, or pharmacologically active salt, derivative, analogue, or prodrug thereof improves one or more pharmacological, physiological, or molecular effects; reduces or alleviates one or more symptoms of the disease or disorder to be treated; or a combination thereof in the subject compared to the same pharmacological, physiological, or molecular effects; or symptoms of the disease or disorder in the subject prior to administration of the fumaric acid ester, or pharmacologically active salt, derivative, analogue, or prodrug thereof to the subject.

In some embodiments, the fumaric acid ester, or pharmacologically active salt, derivative, analogue, or prodrug thereof is administered to a subject in need thereof in an effective amount to improve one or more pharmacological, physiological, or molecular effects, or to reduce or alleviate one or more symptoms of the disease or disorder with higher efficacy, lower toxicity, or a combination thereof compared to a subject treated with an different therapeutic agent such as hydroxyurea (HU).

C. Dosages and Dosage Regimes

For all of the disclosed compounds, as further studies are conducted, information will emerge regarding appropriate dosage levels for treatment of various conditions in various patients, and the ordinary skilled worker, considering the therapeutic context, age, and general health of the recipient, will be able to ascertain proper dosing. The selected dosage depends upon the desired therapeutic effect, on the route of administration, and on the duration of the treatments desired. Generally dosage levels of 0.001 to 100 mg/kg of body weight daily are administered to mammals. Generally, for intravenous injection of infusion, dosage may be lower.

As discussed above some fumaric acid esters have been administered to treat patients for psoriasis and multiple sclerosis.

For example, an exploratory, prospective, open-label study of fumaric acid esters (FAE, FUMADERM) was conducted in patients with relapsing-remitting multiple sclerosis. The study consisted of the following four phases: 6-week baseline, 18-week treatment (target dose of 720 mg/day), 4-week washout, and a second 48-week treatment phase (target dose of 360 mg/day) (Schimrigk, et al., *Eur. J. Neurol.*, 13(6):604-10 (2006)). Following this dosage regime, patients were stable or slightly improved for clinical outcomes including Expanded Disability Status Scale (EDDSS) score, ambulation index (AI), and nine-hole peg test (9-HPT). The most common adverse effects were gastrointestinal symptoms and flushing, and all adverse effects were reported as mild and reversible.

In an exemplary treatment regimen of fumaric acid esters for treatment of psoriasis includes a gradual increase in dosage according to the schedule depicted in Table 3.

TABLE 3

Dosage schedule of fumaric acid esters used for patients with psoriasis (Reproduced from Roll, et al., *Indian J. Dermatol. Venereol. Leprol.*, 73: 133-7 (2007)).

| Week | Fumaderm ® initial | Fumaderm ® | Dosage of DMF |
|---|---|---|---|
| 1 | 1-0-0 | | 30 mg |
| 2 | 1-0-1 | | 60 mg |
| 3 | 1-1-1 | | 90 mg |
| 4 | | 1-0-0 | 120 mg |

TABLE 3-continued

Dosage schedule of fumaric acid esters used for patients with psoriasis (Reproduced from Roll, et al., *Indian J. Dermatol. Venereol. Leprol.*, 73: 133-7 (2007)).

| Week | Fumaderm ® initial | Fumaderm ® | Dosage of DMF |
|---|---|---|---|
| 5 | | 1-0-1 | 240 mg |
| 6 | | 1-1-1 | 360 mg |
| 7 | | 2-1-1 | 480 mg |
| 8 | | 2-1-2 | 600 mg |
| 9 | | 2-2-2 | 720 mg |

This schedule was shown to improve gastrointestinal tolerance (Nast A, et al., *J. German Soc. Dermatol.*, 4:51-5 (2006)). Most patients treated with fumaric acids require two to four tablets of FUMADERM, for treatment of psoriasis.

Therefore, daily dosages for fumaric acid esters can range from about 1 mg to about 5,000 mg, preferably about 10 mg to about 2,500 grams, more preferably about 50 mg to about 2,000 grams of a fumaric acid ester, or a pharmacologically active salt, derivative, analogue or prodrug thereof.

In some embodiments the compositions include DMF, MMF, or a combination thereof. For DMF or MMF, the therapeutically effective amount can range from about 1 mg/kg to about 50 mg/kg (e.g., from about 2.5 mg/kg to about 20 mg/kg or from about 2.5 mg/kg to about 15 mg/kg). Effective doses will also vary, as recognized by those skilled in the art, dependent on route of administration, excipient usage, and the possibility of co-using with other therapeutic treatments including use of other therapeutic agents. For example, an effective dose of DMF or MMF to be administered to a subject, for example orally, can be from about 0.1 g to about 1 g or more than 1 g per day; from about 200 mg to about 800 mg per day; from about 240 mg to about 720 mg per day; from about 480 mg to about 720 mg per day; or about 720 mg per day. The daily dose can be administered in separate administrations of 2, 3, 4, or 6 equal doses.

In some embodiments of the one or more fumaric acid esters, or pharmacologically active salts, derivatives, analogues or prodrugs there are present in a pharmaceutical preparation. In some embodiments the composition is administered to the patient three times per day (TID). In some embodiments the pharmaceutical preparation is administered to the patient two times per day (BID). In some embodiments, the composition is administered at least one hour before or after food is consumed by the patient.

In some embodiments, the composition is administered as part of a dosing regimen. For example, the patient can be administered a first dose of the composition for a first dosing period; and a second dose of the composition for a second dosing period, optionally followed by one or more additional doses for one or more additional dosing periods. The first dosing period can be less than one week, one week or more than one week.

In some embodiments the dosage regime is a dose escalating dosage regime. The first dose can be a low dose. For example, in some embodiments, the composition includes DMF, and a low dose of DMF, for example about 30 mg, can be the starting dose for a dose-escalation protocol. Dose escalation can be continued until a satisfactory biochemical or clinical response is reached. Next, the dosages can be maintained or steadily reduced to a maintenance dose. In some embodiments, the final dosage can be about 1-2 grams per day (i.e., 6 tablets of FUMADERM).

Studies on the use of fumaric acid esters to treat psoriasis show that dosage may not be related to body weight or to the activity of the disease (Nast A, et al., *J. German Soc. Dermatol.*, 4:51-5 (2006)). Accordingly, the dosage and dosage regime for each patient can be adjusted according to the individual's response and the onset of severity of adverse effects.

The most common side effects are gastrointestinal symptoms such as abdominal pain, diarrhea, nausea and malaise. These signs and symptoms occur primarily within the first few weeks after initiation of treatment and within 90 minutes to six hours after oral intake of the drug. They last for several minutes up to half an hour and can be alleviated by intake of tablets with milk.

Flushing of the skin is another common complaint, ranging from rapid sensation of heat to long-lasting facial redness. Improvement of the latter side effect has been see on treatment with acetylsalicylic acid but this has not yet been confirmed scientifically. Typically, the adverse effects discussed above are dose-dependent and they decrease in frequency during the course of the treatment.

Less commonly observed side effects are lymphocytopenia, leukocytopenia and elevated eosinophil counts. A decrease of lymphocytes below $500/mm^3$ should lead to dosage reduction or withdrawal of treatment. The eosinophilia is transient and usually observed between the fourth and tenth week of treatment.

Rarely, moderate elevations of liver enzymes and bilirubin have been observed. Proteinuria has been noted too, but it proved to be transient. An increased risk for infections has not bee documented.

Relapse or rebound phenomena do not typically occur using fumaric acid esters such as FUMADERM. Therefore, treatment may be discontinued abruptly if needed.

The current labeled dosing of hydroxyurea for sickle cell disease calls for the administration of an initial dose of 15 mg/kg/day in the form of a single dose, with monitoring of the patient's blood count every 2 weeks. If the blood counts are in an acceptable range, the dose may be increased by 5 mg/kg/day every 12 weeks until the MTD of 35 mg/kg/day is reached. Pharmaceutical compositions can contain 1 mg/kg to 50 mg/kg of fumaric acid ester, preferably MMF, in combination with 1 mg/kg to 35 mg/kg of HU. The combination formulation can contain 5, 10, 15, 20, 25, 30, 35, 40, 45 or 50 mg/kg of HU.

D. Formulations

Pharmaceutical compositions including a fumaric acid ester, or pharmacologically active salt, derivative, analogue, or prodrug thereof are disclosed. The pharmaceutical compositions may be for administration by oral, parenteral (intramuscular, intraperitoneal, intravenous (IV) or subcutaneous injection), transdermal (either passively or using iontophoresis or electroporation), or transmucosal (nasal, vaginal, rectal, or sublingual) routes of administration or using bioerodible inserts and can be formulated in unit dosage forms appropriate for each route of administration.

Red blood cells, which are cells of erythroid lineage, are the primary producers of hemoglobin. Therefore, in a preferred embodiment the fumaric acid esters are administered to a subject in an effective amount to induce HbF in hematopoietic stems cells. In the early fetus, erythropoiesis takes place in the mesodermal cells of the yolk sac. By the third or fourth month, erythropoiesis moves to the spleen and liver. After seven months, erythropoiesis occurs primarily in the bone marrow, however, in certain disease states erythropoiesis can also occurs outside the bone marrow, within the spleen or liver, in adults. Therefore, in some embodiments, the compositions are administered in an effective amount to induce HbF expression in cells of erythroid lineage in the bone marrow (i.e., the red bone marrow), the liver, the spleen, or combinations thereof.

Preferably the composition induces HbF in cells synthesizing or committed to synthesize hemoglobin. For example, in preferred embodiments, the fumaric acid ester, or pharmacologically active salt, derivative, analogue, or prodrug thereof induces HbF in basophilic normoblast/early normoblast also commonly called erythroblast, polychromatophilic normoblast/intermediate normoblast, orthochromatic normoblast/late normoblast, or a combination thereof.

In a preferred embodiment, the composition is an oral formulation. Oral formulations of DMF or MMF such as FUMADERM can be absorbed by the small intestine where MMF can enter systemic circulation.

In some embodiments, the composition is administered locally, to the site in need of therapy. Although red blood cells are the primary producers of hemoglobin, reports indicate that other, non-hematopoietic cells, including macrophage, retinal, pigment cells, and alveolar epithelial cells such as alveolar typeII (ATII) cells and Clara cells which are the primary producers of pulmonary surfactant, also synthesize hemoglobin (Newton, et al., *J. Biol. Chem.*, 281(9) 5668-5676 (2006), Tezel, et al., *Invest. Ophthalmol. Vis. Sci.*, 50(4):1911-9 (2009), Liu, et al., *Proc. Natl. Acad. Sci. USA*, 96(12)6643-6647 (1999)). These findings are consistent with the conclusion that the expression of hemoglobin by non-erythroid cells at interfaces where oxygen-carbon dioxide diffusion occurs may be an adaptive mechanism to facilitate oxygen transport.

Therefore, in some embodiments, the composition is administered locally to interfaces where oxygen-carbon dioxide diffusion occurs, including but not limited, to the eye or lungs.

In some embodiments, the composition is administered locally to the eye to treat a retinopathy, or another ocular manifestation associated with sickle cell disease, or a related disorder.

1. Formulations for Enteral Administration

In a preferred embodiment the compositions am formulated for oral delivery. Oral solid dosage forms are described generally in Remington's Pharmaceutical Sciences, $18^{th}$ Ed. 1990 (Mack Publishing Co. Easton Pa. 18042) at Chapter 89. Solid dosage forms include tablets, capsules, pills, troches or lozenges, cachets, pellets, powders, or granules or incorporation of the material into particulate preparations of polymeric compounds such as polylactic acid, polyglycolic acid, etc., or into liposomes. Such compositions may influence the physical state, stability, rate of in vivo release, and rate of in vivo clearance of the disclosed. See, e.g., Remington's Pharmaceutical Sciences, $18^{th}$ Ed. (1990, Mack Publishing Co., Easton, Pa. 18042) pages 1435-1712 which are herein incorporated by reference. The compositions may be prepared in liquid form, or may be in dried powder (e.g., lyophilized) form. Liposomal or proteinoid encapsulation may be used to formulate the compositions. Liposomal encapsulation may be used and the liposomes may be derivatized with various polymers (e.g., U.S. Pat. No. 5,013, 556). See also, Marshall, K. In: Modern Pharmaceutices Edited by G. S. Banker and C. T. Rhodes Chapter 10, 1979. In general, the formulation will include the peptide (or chemically modified forms thereof) and inert ingredients which protect peptide in the stomach environment, and release of the biologically active material in the intestine.

The fumaric acid ester, or pharmacologically active salt, derivative, analogue, or prodrug thereof may be chemically modified so that oral delivery of the compound is efficacious. Generally, the chemical modification contemplated is the attachment of at least one moiety to the component molecule itself, where the moiety permits uptake into the blood stream from the stomach or intestine, or uptake directly into the intestinal mucosa. Also desired is the increase in overall stability of the component or components and increase in circulation time in the body. PEGylation is a preferred chemical modification for pharmaceutical usage. Other moieties that may be used include: propylene glycol, copolymers of ethylene glycol and propylene glycol, carboxymethyl cellulose, dextran, polyvinyl alcohol, polyvinyl pyrrolidone, polyproline, poly-1,3-dioxolane and poly-1,3,6-tioxocane [see, e.g., Abuchowski and Davis (1981) "Soluble Polymer-Enzyme Adducts," in Enzymes as Drugs. Hocenberg and Roberts, eds. (Wiley-Interscience: New York, N.Y.) pp. 367-383; and Newmark, et al. (1982) J. Appl. Biochem. 4:185-189].

Another embodiment provides liquid dosage forms for oral administration, including pharmaceutically acceptable emulsions, solutions, suspensions, and syrups, which may contain other components including inert diluents; adjuvants such as wetting agents, emulsifying and suspending agents; and sweetening, flavoring, and perfuming agents.

Controlled release oral formulations may be desirable. Fumaric acid esters, or pharmacologically active salt, derivatives, analogues, or prodrugs thereof can be incorporated into an inert matrix which permits release by either diffusion or leaching mechanisms, e.g., gums. Slowly degenerating matrices may also be incorporated into the formulation. Another form of a controlled release is based on the Oros therapeutic system (Alza Corp.) i.e., the drug is enclosed in a semipermeable membrane which allows water to enter and push drug out through a single small opening due to osmotic effects.

For oral formulations, the location of release may be the stomach, the small intestine (the duodenum, the jejunem, or the ileum), or the large intestine. Preferably, the release will avoid the deleterious effects of the stomach environment, either by protection of the agent (or derivative) or by release of the agent (or derivative) beyond the stomach environment, such as in the intestine. To ensure full gastric resistance a coating impermeable to at least pH 5.0 is essential. Examples of the more common inert ingredients that are used as enteric coatings are cellulose acetate trimellitate (CAT), hydroxypropylmethylcellulose phthalate (HPMCP), HPMCP 50, HPMCP 55, polyvinyl acetate phthalate (PVAP), Eudragit L30D™, Aquateric™, cellulose acetate phthalate (CAP), Eudragit L™, Eudragit S™, and Shellac™. These coating may be used as mixed films.

2. Topical or Mucosal Delivery Formulations

Compositions can be applied topically, the compositions can be delivered to the lungs while inhaling and traverses across the lung epithelial lining to the blood stream when delivered either as an aerosol or spray dried particles having an aerodynamic diameter of less than about 5 microns.

A wide range of mechanical devices designed for pulmonary delivery of therapeutic products can be used, including but not limited to nebulizers, metered dose inhalers, and powder inhalers, all of which are familiar to those skilled in the art. Some specific examples of commercially available devices are the Ultravent™ nebulizer (Mallinckrodt Inc., St. Louis, Mo.); the Acorn II™ nebulizer (Marquest Medical Products, Englewood, Colo.); the Ventolin™ metered dose inhaler (Glaxo Inc., Research Triangle Park, N.C.); and the Spinhaler™ powder inhaler (Fisons Corp., Bedford, Mass.).

Formulations for administration to the mucosa will typically be spray dried drug particles, which way be incorporated into a tablet, gel, capsule, suspension or emulsion. Standard pharmaceutical excipients are available from any formulator. Oral formulations may be in the form of chewing gum, gel strips, tablets or lozenges.

Transdermal formulations may also be prepared. These will typically be ointments, lotions, spray, or patches, all of which can be prepared using standard technology. Transdermal formulations will require the inclusion of penetration enhancers.

3. Controlled Delivery Polymeric Matrices

Controlled release polymeric devices can be made for long term release systemically following implantation of a polymeric device (rod, cylinder, film, disk) or injection (microparticles). The matrix can be in the form of microparticles such as microspheres, where peptides are dispersed within a solid polymeric matrix or microcapsules, where the core is a different material than the ploymeric shell, and the peptide is dispersed or suspended in the core, which may be liquid or solid in nature. Unless specifically defined herein, microparticles, microspheres, and microcapsules are used interchangeably. Alternatively, the polymer may be cast as a thin slab or film, ranging from nanometers to four centimeters, a powder produced by grinding or other standard techniques, or even a gel such as a hydrogel.

Either non-biodegradable or biodegradable matrices can be used for delivery of disclosed compounds, although biodegradable matrices are preferred. These may be natural or synthetic polymers, although synthetic polymers are preferred due to the better characterization of degradation and release profiles. The polymer is selected based on the period over which release is desired. In some cases linear release may be most useful, although is others a pulse release or "bulk release" may provide more effective results. The polymer may be in the form of a hydrogel (typically in absorbing up to about 90% by weight of water), and can optionally be crosslinked with multivalent ions or polymers.

The matrices can be formed by solvent evaporation, spray drying, solvent extraction and other methods known to those skilled in the art. Bioerodible microspheres can be prepared using any of the methods developed for making microspheres for drug delivery, for example, as described by Mathiowitz and Langer, J. Controlled Release 5:13-22 (1987); Mathiowitz, et al., Reactive Polymers 6:275-283 (1987); and Mathiowitz, et al., J. Appl. Polymer Sci. 35:755-774 (1988).

The devices can be formulated for local release to treat the area of implantation or injection—which will typically deliver a dosage that is much less than the dosage for treatment of an entire body—or systemic delivery. These can be implanted or injected subcutaneously, into the muscle, fat, or swallowed.

IV. Methods of Diagnosis

The methods of treatment disclosed herein can include a first step of selecting a subject for treatment. In some embodiments, the subject is selected for treatment when the subject exhibits one or more of the clinical symptoms of sickle cell disease, beta-thalassemia, or a related disorder such as those discussed above. In some embodiments, the subject is selected for treatment when the subject exhibits a genetic or biochemical indicator of sickle cell disease, beta-thalassemia, or a related disorder. For example, the subject can be selected for treatment based on identification of a genetic alteration, defect, or mutation in the beta-globin gene or an expression control sequence thereof, by biochemical or morphological alterations in hemoglobin or hemoglobin synthesizing cells, or combinations thereof.

In a some embodiments, the subject is selected when a combination of clinical symptoms and genetic or biochemical alterations are identified. In some embodiments, the subject is selected based on one or more clinical symptoms, or one or more genetic or biochemical alterations. For example, subjects can be selected for treatment based on the identification of a genetic alteration, a biochemical or morphological alteration, or a combination thereof, before the subject exhibits clinical symptoms of sickle cell disease, beta-thalassemia, or a related disorder.

A. Identification of Genetic Alterations

In some embodiments, the subject is selected for treatment based on identification of one or more genetic alterations in one or more alleles of the human beta-globin gene or expression control sequence thereof. Genetic alterations indicative of sickle cell disease, beta-thalassemia, or related disorders include the exemplary mutations discussed above, or other mutations that lead to a reduction in the synthesis, structure, or function of human beta-globin protein.

Methods of selecting subject having one or more genetic alterations in one or more alleles of the beta-globin gene or expression control sequences thereof include the steps of obtaining a biological sample containing nucleic acid from the subject and detecting the presence or absence one or more genetic alterations in one or more alleles of the beta-globin gene or expression control sequences thereof in the biological sample. Any biological sample that contains the DNA of the subject to the diagnosed can be employed, including tissue samples and blood samples, with nucleated blood cells being a particularly convenient source. The DNA may be isolate from the biological sample prior to testing the DNA for the presence of absence of the genetic alterations.

The detecting step can include determining whether the subject is heterozygous or homozygous for a genetic alteration. The step of detecting the presence or absence of the genetic alteration can include the step of detecting the presence or absence of the alteration in both chromosomes of the subject (i.e., detecting the presence or absence of one or two alleles containing the marker or functional polymorphism). More than one copy of a genetic alterations (i.e., subjects homozygous for the genetic marker) can indicate a greater risk of developing sickle cell disease, beta-thalassemia, or related disorder. In some embodiments, the subject is heterozygous for two or more genetic alterations in the beta-globin gene (also referred to herein as double heterozygotes, triple heterozygotes, etc.). One copy of two or more genetic alterations in the beta-globin gene can indicate a greater risk of developing sickle cell disease, beta-thalassemia, or related disorder.

The process of determining the genetic sequence of human beta-globin gene is referred to as genotyping. In some embodiments, the human beta-globin gene is sequenced. Methods for amplifying DNA fragments and sequencing them are well known in the art. For example, automated sequencing procedures that can be utilized to sequence the beta-globin gene, include, but not limited to, sequencing by mass spectrometry single-molecule real-time sequencing (Pacific Bio), ion semiconductor (ion torrent sequencing), pyrosequencing (454), sequencing by synthesis (Illumina), sequencing by ligation (SOLiD sequencing), chain termination (Sanger sequencing).

In some embodiments, the genotype of the subject is determined by identifying the presence of one or more single nucleotide polymorphisms (SNP) associated with sickle cell disease, beta-thalassemia, or a related disorder. Methods for SNP genotyping are generally known in the art (Chen et al., *Pharmacogenomics J.*, 3(2):77-96 (2003); Kwok, et al., *Curr. Issues Mol. Biol.*, 5(2):43-60 (2003); Shi, *Am. J. Pharmacogenomics*, 2(3); 197-205 (2002); and Kwok, *Annu. Rev. Genomics Hum. Genet.*, 2:235-58 (2001)).

SNP genotyping can include the steps of collecting a biological sample from a subject (e.g., sample of tissues, cells, fluids, secretions, etc.), isolating genomic DNA from the cells of the sample, contacting the nucleic acids with one or more primers which specifically hybridize to a region of the isolated nucleic acid containing a target SNP under conditions such that hybridization and amplification of the target nucleic acid region occurs, and determining the nucleotide present at the SNP position of interest, or, in some assays, detecting the presence or absence of an amplification product (assays can be designed so that hybridization and/or amplification will only occur if a particular SNP allele is present or absent). In some assays, the size of the amplification product is detected and compared to the length of a control sample; for example, deletions and insertions can be detected by a change in size of the amplified product compared to a normal genotype.

The neighboring sequence can be used to design SNP detection reagents such as oligonucleotide probes and primers. Common SNP genotyping methods include, but are not limited to, TaqMan assays, molecular beacon assays, nucleic acid arrays, allele-specific primer extension, allele-specific PCR, arrayed primer extension, homogeneous primer extension assays, primer extension with detection by mass spectrometry, pyrosequencing, multiplex primer extension sorted on genetic arrays, ligation with rolling circle amplification, homogeneous ligation, multiplex ligation reaction sorted on genetic arrays, restriction-fragment length polymorphism, single base extension-tag assays, and the Invader assay. Such methods may be used in combination with detection mechanisms such as, for example, luminescence or chemiluminescence detection, fluorescence detection, time-resolved fluorescence detection, fluorescence resonance energy transfer, fluorescence polarization, mass spectrometry, and electrical detection.

Other suitable methods for detecting polymorphisms include methods in which protection form cleavage agents is used to detect mismatched bases in RNA/RNA or RNA/DNA duplexes (Myers et al., *Science*, 230:1242 (1985); Cotton, et al., *PNAS*, 85:4397 (1988); and Saleeba, et al., *Meth. Enzymol.*, 217:286-295 (1992)), comparison of the electrophoretic mobility of variant and wild type nucleic acid molecules (Orita et al., *PNAS*, 86:2766 (1989); Cotton, et al. *Mutat. Res.*, 285:125-144 (1993); and Hayashi, et al., *Genet. Anal. Tech. Appl.*, 9:73-79 (1992)), and assaying the movement of polymorphic or wild-type fragments in polyacrylamide gels containing a gradient of denaturant using denaturing gradient gel electrophoresis (DGGE) (Myers et al., *Nature*, 313:495 (1985)). Sequence variations at specific locations can also be assessed by nuclease protection assays such as Rnase and S1 protection or chemical cleavage methods.

Another method for genotyping SNPs is the use of two oligonucleotide probes in an oligonucleotide ligation assay (OLA) (U.S. Pat. No. 4,988,617). In this method, one probe hybridizes to a segment of a target nucleic acid with its 3'-most end aligned with the SNP site. A second probe hybridizes to an adjacent segment of the target nucleic acid molecule directly 3' to the first probe. The two juxtaposed probes hybridize to the target nucleic acid molecule, and are ligated in the presence of a linking agent such as a ligase if there is perfect complementarity between the 3'-most nucleotide of the first probe with the SNP site. If there is a mismatch, ligation would not occur. After the reaction, the ligated probes are separated from the target nucleic acid molecule, and detected as indicators of the presence of a SNP.

Other methods that can be used to genotype the SNPs include single-strand conformational polymorphism (SSCP), and denaturing gradient gel electrophoresis (DGGE). SSCP identifies base differences by alteration in electrophoretic migration of single stranded PCR products. Single-stranded PCR products can be generated by heating or otherwise denaturing double stranded PCR products. Single-stranded nucleic acids may refold or form secondary structures that are partially dependent on the base sequence. The different electrophoretic mobilities of single-stranded amplification products are related to base-sequence differences at SNP positions. DGGE differentiates SNP alleles based on the different sequence-dependent stabilities and melting properties inherent in polymorphic DNA and the corresponding differences in electrophoretic migration patterns in a denaturing gradient gel.

Sequence-specific ribozymes (U.S. Pat. No. 5,498,531) can also be used to score SNPs based on the development or loss of a ribozyme cleavage site. Perfectly matched sequences can be distinguished from mismatched sequences by nuclease cleavage digestion assays or by differences in melting temperature. If the SNP affects a restriction enzyme cleavage site, the SNP can be identified by alterations in restriction enzyme digestion patterns, and the corresponding changes in nucleic acid fragment lengths determined by gel electrophoresis.

B. Identification of Biochemical and Morphological Alterations

In some embodiments, subjects are selected for treatment based on identification of biochemical or morphological alterations or abnormalities in hemoglobin, or hemoglobin synthesizing cells such as hematopoietic stem cells, erythrocyte progenitor cells, erythrocytes, macrophage, retinal pigment epithelial cells, alveolar type II (ATII) cells, and others. The methods typically include identifying one or more biochemical or morphological alterations that is associated with a genetic alteration in the human beta-globin gene, or otherwise diagnostic of sickle cell disease, a beta-thalassemia, or a related disorder. Methods of diagnosing sickle cell disease, beta-thalassemia, or a related disorder according to biochemical or morphological alterations in the hemoglobin or hemoglobin synthesizing cells are known in the art, and include but are not limited to, analysis of erythrocyte morphology, osmotic fragility, hemoglobin composition, globin synthetsis rates, and red blood cell indices (Rowley, *American Journal of Hematology,* 1(1): 129-137, (1976)).

In some embodiments, the method includes testing a subject's blood for HbS, and selecting the subject for treatment if HbS is present. Methods for testing a subject's blood for the presence of HbS include solubility tests (e.g., SICKLEDEX) and sickling test. The SICKLEDEX test operates on the principle that Hb-S tends to form tactoids or liquid crystals within the erythrocytes under conditions of low oxygen tension resulting in the characteristic "sickle shape" distortion of the red cell. A reducing agent (i.e., dithionite) is mixed with whole blood and buffer. If Hb-S is present, it becomes insoluble and forms a cloudy suspension. Other hemoglobins are more soluble and will form a transparent solution. A sickling test can be used to determine if a red blood cell changes into a sickle shape after a blood sample is mixed with a reducing agent and identifying morphological changes to shape of red blood cells (i.e., "sickling") by microscopy.

Other suitable tests include, hemoglobin electrophoresis, which employs gel electrophoretic techniques to separate out the various types of hemoglobin from a blood sample obtained from the subject. The test can detect abnormal levels of HbS, as well as other abnormal hemoglobins, such as hemoglobin C. It can also be used to determine whether there is a deficiency of any normal form of hemoglobin, as in various thalassemias. Alternatives to electrophoretic techniques include isoelectric focusing and chromatographic techniques.

Other tests that can be used to select a subject for treatment with the compositions and methods disclosed herein include tests typically employed as part of a hemolglobinopathy screen, for example, a complete blood count (CBS) or iron study (ferritin). For example, a blood count can be used to detect anemia, and a blood smear and be used to identify sickled cells.

EXAMPLES

Example 1: Monomethylfumarate (MMF) Induces γ-Globin (Hbf) Gene and Protein Expression in Cells of Erythroid Lineage Materials and Methods Pharmaceutical Agents The fumaric acid esters dimethylfumarate (DMF) and monomethylfumarate (MMF) are the primary constituents of Fumaderm and BG00012, drugs currently marketed for treatment of psoriasis. BG00012 is also completing phase III clinical testing for treatment of multiple sclerosis. MMF is the major bioactive component of each.

Cell Culture

KU812, a human leukemic cell line that expresses the fetal γ-globin and adult β-globin genes, is a commonly used system for screening and discovery of novel HbF inducers; this is because of comparable globin gene response patterns in KU812 and primary erythroid cells after treatments with drug inducers.

Results

KU812 cells were cultured in the presence or absence of MMF for time periods ranging from 0-24 hours and evaluated for changes in γ-globin gene expression relative to 18S ribosomal RNA expression (internal experimental control) by qPCR (FIG. 1). In comparison to control, untreated (UT) cells, significant increases in γ-globin gene expression were observed as early as 3 hours post-incubation with low-does (100 μM) MMF treatment. This MMF-induced increase in γ-globin expression persisted up to 24 h post-exposure to the compound. Data in FIG. 1 are represented as means±standard error of the mean (SEM); *$P<0.05$, $P<0.01$ and *$P<0.001$.

Figure 2:
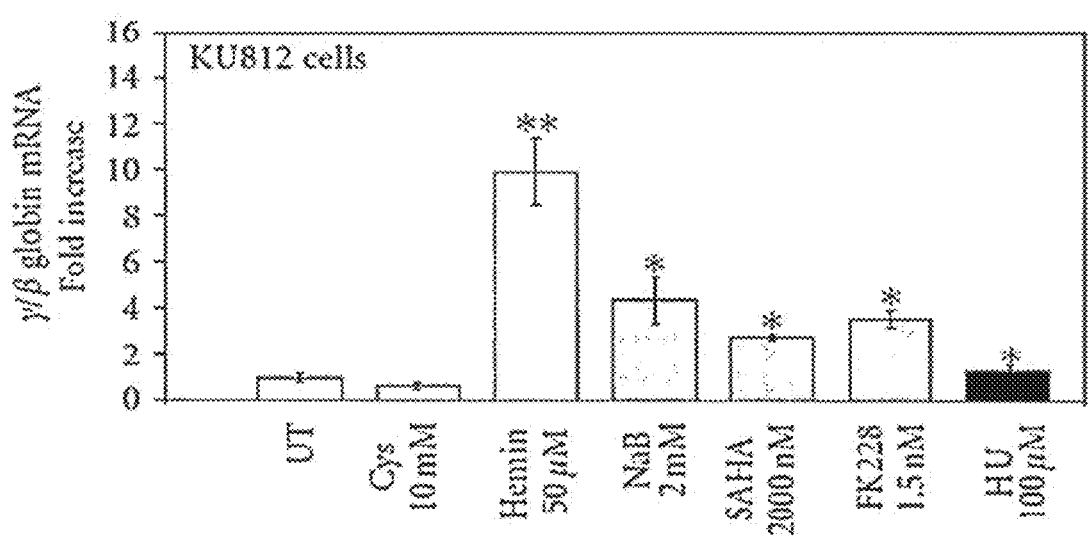
FIG. 2 is a bar graph showing the change in γ/β-globin mRNA expression (fold change compared to untreated control ("UT")) in KU812 cells over time (hours) following treatment with known fetal hemoglobin (HbF) inducers (10 mM Cysteine (Cys), 50 µM Hemin, 2 mM sodium buytrate NaB, 2000 nM suberoylanilide hydroxamic acid (SAHA), 105 nM cyclic peptide FK228 (depsipeptide), 100 µM hydroxyurea (HU)). Reproduced from Makala, et al., *Anemia*. 2012; 2012:428137. Epub 2012 May 14.

FIG. 1 shows that 100 μM MMF increases the expression of γ-globin gene expression in KU812 cells ~2-4-fold depending upon the incubation time. FIG. 2 shows the induction of γ-globin transcription by known HbF inducers in KU812 cells cultured under conditions similar to those described above. FIG. 2 is reproduced from MaKala et al., *Anemia*, Volume 2012, Article ID 428137) (2012). The last bar of FIG. 2 shows data for hydroxyurea (HU). At 100 μM, the same concentration that we used for MMF, HU induces γ-globin gene expression ~2-fold. This data supports the conclusion that MMF is at least equivalent, or even better than HU, in terms of its ability to induce γ-globin gene expression in this cell system.

Example 2: Monomethylfumarate (MMF) Drives Expression by Activation the γ-Globin (Hbf) Gene Promoter Materials and Methods
From MaKala et al., *Anemia*, Volume 2012, Article ID 428137) (2012)

KU812 Stable Lines

KU812 stable cell lines were created by co-transfecting wild-type KU812 cells with pEGFP-NI (G418 selectable marker) and the μLCRβprRluc AγprFluc dual reporter a kind gifts from Dr. George Stamatoyannopoulos (University of Washington). Briefly, the 315-bp human β-globin gene promoter sequence was inserted upstream of the Renilla along with a polyadenylation signal downstream to create PβprRluc. Likewise, 1.4 kb of human αγ-globin promoter was inserted upstream of firefly luciferase to create AγprFluc. The μLCR (locus control region), PβprRluc, and AγprFluc fragments were subsequently cloned into the mammalian vector, pRL-null. The dual-luciferase reporter lines were produced using 10 μg each of linearized μLCRβprRluc AγprFluc and pEGFP-NI plasmids co-transfected into KU812 cells by electroporation at 260 V, 975 μF (Bio-Rad, Hercules Calif.). After 72 hr, G418 was added at a concentration of 900 μg/μl for 3 days then maintained under selection pressure indefinitely at a concentration of 400 μg/μl. KU812 stable lines were treated with the various drugs at the same concentrations described above. FK228 and analogues were screened at concentrations between 1-1000 nM for 48 hr and cell toxicity was monitored by 2% Trypan blue exclusion. The effect of drug treatments on γ-globin and β-globin promoter activity was monitored by luciferase assay.

Dual Luciferase Assay

Luciferase activity was monitored under the different experimental conditions using the Dual Luciferase Assay Reporter System (Promega, Madison, Wis.). The activity of firefly luciferase represents γ-globin promoter activity (γF), while the renilla luciferase is the read-out for β-globin promoter activity (βR). The β-globin promoter was strategically cloned between the LCR and γ-globin promoter to increase β expression, while simultaneously increasing the sensitivity of detection of γ-globin gene inducers. After drug treatments, KU812 stable cells were washed with 1× phosphate buffered saline and lysed in 1× Passive Lysis Buffer for 15 min, then protein extracts were added to the Luciferase Assay Reagent II and firefly luciferase activity quantified in a Turner Designs TD-20/20 luminometer (Sunnyvale, Calif.). To measure βR activity, Stop & Glo Reagents was added to measure the renilla luciferase activity. Total protein was determined by Bradford assay on a Beckman DU 640 spectrophotometer (Chaska, Minn.) and luciferase activity was corrected for total protein.

Results

The fumaric acid ester was also in the KU812 dual-luciferase reporter system, an assay system using a stable KU812 cell line created with the μLCRβprRlucγprFluc construct containing a 3.1-kb μLCR cassette linked to a 315-bp human β-globin promoter driving the renilla and a 1.4-kb Aγ-globin promoter driving the firefly luciferase genes. Since, the firefly luciferase gene (γF) has approximately 50% greater luminescence than the renilla gene (βR), renilla activity was multiplied by two to adjust for the difference in luminescence yielding the γ/γ+2β final measurement. This assay system was previously reported as an efficacious screening tool for the identification of γ-globin gene activators (MaKala et al., *Anemia*, Volume 2012, Article ID 428137) (2012)).

Figure 3:
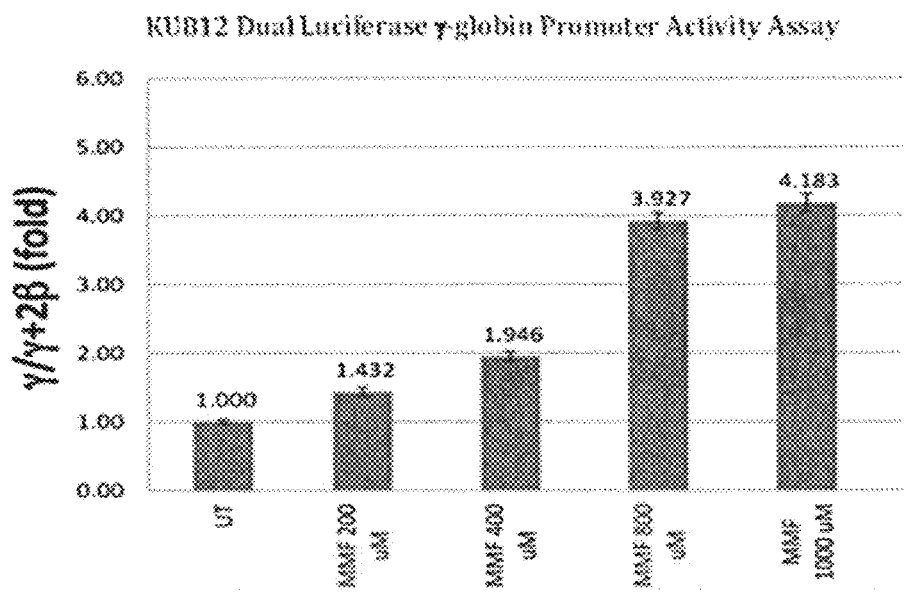
FIG. 3 is a bar graph showing the ratio of luciferase gene expression (γ) to γ+2× gene expression (γ+2β) (fold change compared to untreated control ("UT")) in KU812 cells over time (hours) treated with increasing doses of monomethylfumarate (MMF). The assayed KU812 cells express a µLCRβprRlucγprFluc construct containing a 3.1-kb µLCR cassette linked to a 315-bp human β-globin promoter driving the renilla and a 1.4-kb Aγ-globin promoter driving the firefly luciferase genes.

Luciferase activity, an indicator of γ-globin promoter induction, was monitored KU812 μLCRβprRlucγprFluc—stable cells cultured in the presence of absence (untreated control, UT) of MMF at varying dosages for 48 hour according to the method discussed above and in MaKala et al., *Anemia*, Volume 2012, Article ID 428137) (2012). MMF induced γ-globin promoter activity in a dose-dependent manner (FIG. 3). Cell viability by Trypan blue exclusion remained at 90-95% for the concentrations shown, indicating that even at higher concentrations, MMF exhibits little or no cellular toxicity.

Figure 4:
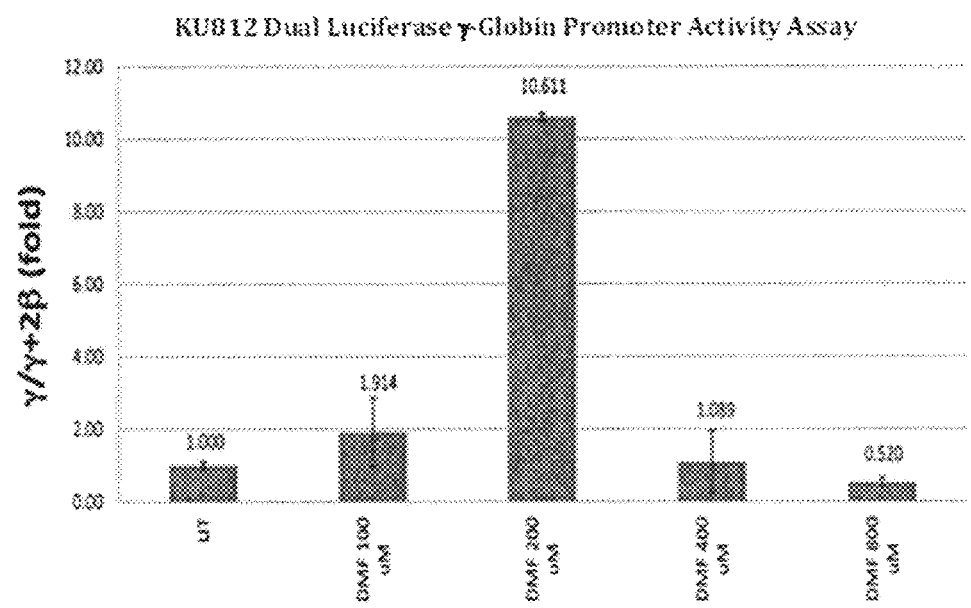
FIG. 4 is a bar graph showing the ratio of luciferase gene expression (γ) to γ+2× renilla gene expression (γ+2β) (fold change compared to untreated control ("UT")) in KU812 cells over time (hours) treated with increasing doses of dimethylfumarate (DMF). The assayed KU812 cells express a µLCRβprRlucγprFluc construct containing a 3.1-kb µLCR cassette linked to a 315-bp human β-globin promoter driving the renilla and a 1.4-kb Aγ-globin promoter driving the firefly luciferase genes.

Example 3: Dimethylfumarate (DMF) Drives Expression by Activation the γ-Globin (Hbf) Gene Promoter MMF is the primary bioactive metabolite derived from metabolism of FUMADERM and BG00012, the fumaric acid ester drugs presently used clinically, and DMF is the primary ingredient. Therefore, the effectiveness of DMF was tested as an inducer of γ-globin gene expression under experimental conditions identical to those described above in Example 2. As with MMF, treatment of cells with DMF also induced γ-globin promoter activity significantly (FIG. 4). At concentrations in the 100-200 μM range, induction of γ-globin promoter activity increased ~2-10 fold in comparison to control, untreated (UT) cells. However, at higher concentrations the effectiveness of DMF as an inducer of γ-globin promoter activity declined substantially. Trypan blue exclusion revealed that this decrease was likely due to an increase in cellular toxicity as indicated by a decrease in cell viability.

Figure 5:
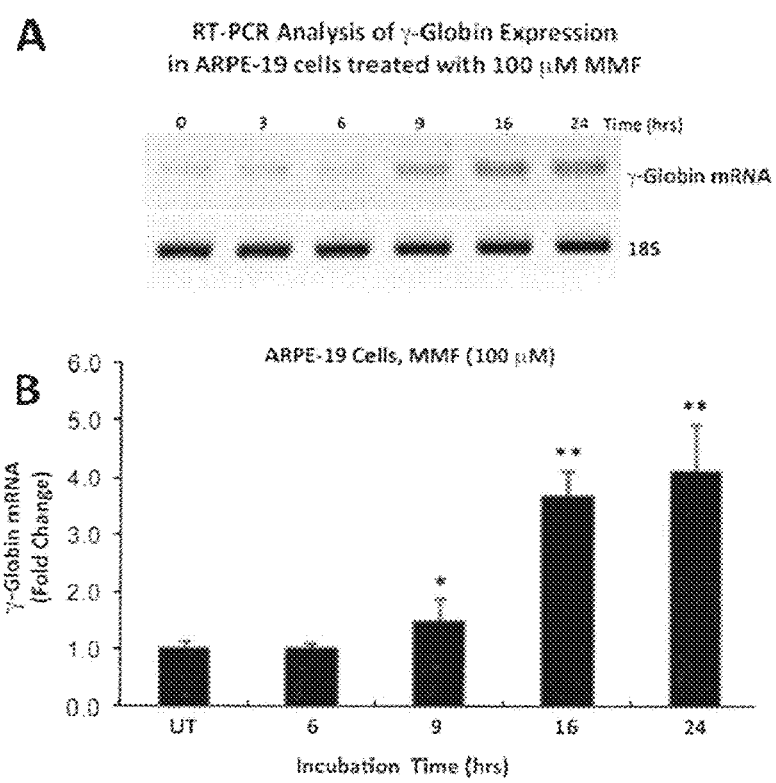
FIG. 5A is a photograph of a gel showing γ-globin expression in human RPE cells (ARPE-19 cell line) analyzed by reverse transcriptase-polymerase chain reaction (RT-PCR) at various time points after treatment with 100 μM monomethylfumarate (MMF).
FIG. 5B is a bar graph showing γ-globin expression in human RPE cells (ARPE-19 cell line) analyzed by real-time quantitative PCR (qPCR) at various time points after treatment with 100 μM monomethylfumarate (MMF). Data are represented as mean±SEM; *$P<0.05$, **$P<0.01$.

Example 4: Monomethylfumarate (MMF) Induces γ-Globin (Hbf) Gene and Protein Expression in a Retinal Pigment Ephithelial (RPE) Cell Line Red blood cells, cells of erythroid lineage, are the primary producers of hemoglobin. However, recent reports suggest that other, non-hematopoietic cells are capable of the same. This includes retinal pigment epithelial (RPE) cells, a cell type critical to normal visual function. Therefore, an assay was designed to test the induction of γ-globin gene expression by MMF in ARPE-19, a transformed human RPE cell line commonly used as an in vitro model of human RPE ARPE-19 cells were cultured in the presence or absence of MMF (100 μM) for varying periods of time (0-24 h) and the expression of γ-globin analyzed by reverse transcriptase-polymerase chain reaction. (RT-PCR) (FIG. 5A). A time-dependent increase in γ-globin gene expression was observed in these cells when cultured in the presence of MMF.

The results presented in FIG. 5A were data were corroborated using real-time quantitative PCR (qPCR) (FIG. 5B). Data are represented as mean±SEM; *P<0.05, **P<0.01.

Immunofluorescence localization techniques utilizing a FITC-labeled anti-HbF antibody confirmed that the MMF-induced increase in γ-globin mRNA was associated with a corresponding increase in HbF protein expression.

Figure 6:
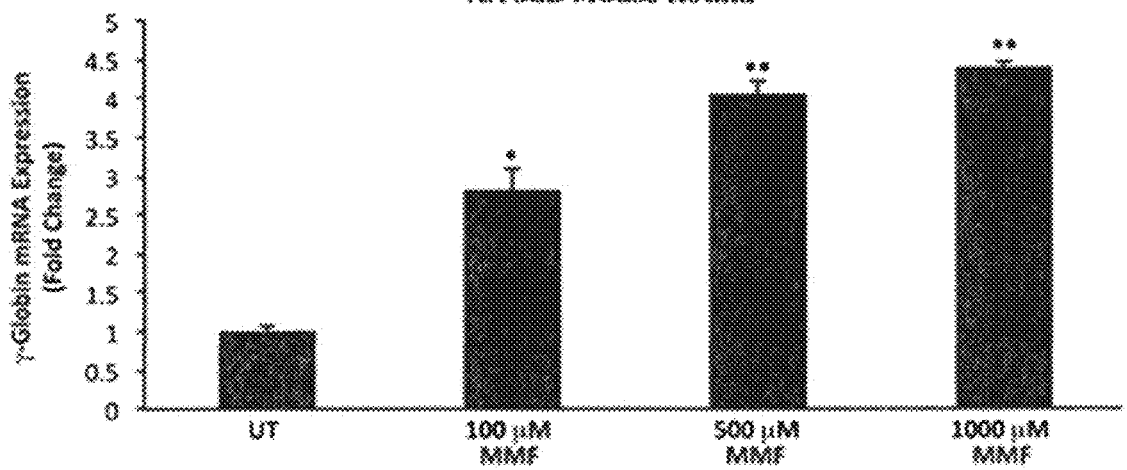
FIG. 6 is a bar graph showing γ-globin mRNA expression in primary RPE cells (fold change) isolated from the eyes of humanized mice analyzed by real-time quantitative PCR (qPCR) following treatment with monomethylfumarate (MMF) at various concentrations ranging from 0-1000 μM for a period of 9 hours. Data are represented as mean±SEM; *$P<0.01$, **$P<0.001$.

Example 5: Monomethylfumarate (MMF) Induces γ-Globin (Hbf) Gene and Protein Expression in Primary Retinal Pigment Epithelial (RPE) Cells The effect of MMF on primary RPE cells was also investigated. RPE cells were isolated from the eyes of humanized mice and used to establish primary RPE cell cultures. These animals have been genetically engineered such that they express human rather than mouse beta and gamma globin genes and hence synthesize human hemoglobin. Primary RPE cells were cultured in the presence or absence of MMF at concentrations ranging from 0-1000 μM for a period of 9 hours. Total RNA was prepared and γ-globin gene expression analyzed by qPCR. A dose-dependent increase in γ-globin gene expression was observed also in these cells when cultured in the presence of MMF (0-1000 μM) (FIG. 6). Data are represented as mean±SEM; *P<0.01, **P<0.001.

Example 6: Evaluation of the Induction of γ-Globin by DMF and MMF

Methods and Materials

Induction of γ-globin by DMF and MMF (Sigma, St. Louis, Mo.) in the dual-luciferase KU812 stable line using a dual luciferase assay was investigated. HU (100 μM; Sigma) was included as a positive control and cell viability was monitored by trypan blue exclusion. Findings in KU812 cells were confirmed in human primary erythroid progenitor cells grown in liquid culture using a published protocol. Globin expression was measured by qPCR also as previously published. HbF protein was measured relative to that of isotype control using FITC conjugated anti-human HbF antibody (1:1000; Santa Cruz Biotechnology, Santa Cruz, Calif.) and fluorescence activated cell sorting (see supplemental methods for details). HbF protein expression was confirmed by Western blot analysis using anti-human HbF antibody (1:1000; Bethyl Laboratories, Inc., Montgomery, Tex.) and horseradish peroxidase-conjugated sheep IgG (1:1000; Santa Cruz).

Identical experiments were performed using the human RPE cell line ARPE-19, an established model for the study of RPE19, and primary RPE cell cultures established from the eyes of HbAA- and HbSS-expressing Townes humanized knock-in SCD mice (Jackson Laboratories, Bar Harbor, Me.) per our published method. Additionally, MMF (1 mM final concentration) or PBS (control) was injected intravitreally into the eyes of HbAA and HbSS mice and retinal γ-globin and HbF expression analyzed by qPCR and immunofluorescence 24 h post-injection. Animal studies were approved by the Georgia Regents University Institutional Committee for Animal Use in Research and Education.

Primary Erythroid Culture

Erythroid progenitors were generated in vitro from adult CD34$^+$ stem cells (STEMCELL technologies, Inc. Vancouver, Canada) using a 2-stage culture system that achieves terminal erythroid differentiation$_{18}$. CD34$^+$ stem cells (500,000) were grown in First medium consisting of Iscove Modified Dulbecco Media containing human AB serum, interleukin-3 (10 ng/mL), stem cell factor (10 ng/mL) and erythropoietin (2 IU/mL). On day 7, the erythroblasts were placed in Second medium with 2 IU/mL erythropoietin for the duration. On day 8, erythroid cells were treated with monomethylfumarate (MMF, 1000 μM), dimethylfumarate (DMF, 200 μM) or hydroxyurea (HU, 100 μM). Then cells were harvested for total RNA and protein for qPCR, FACS and western blot analyses.

Fluorescence Activated Cell Sorting (FACS)

After drug treatments, 500,000 cells were washed twice with phosphate buffered saline and then fixed in 4% paraformaldehyde and permeated with ice-cold acetone/methanol (4:1). Cells were incubated with anti-γ-globin-FITC antibody (Santa Cruz Biotechnology, Santa Cruz, Calif.) in PBT (PBS/01% BSA/0.1% triton X100) solution for 20 min to stain intracellular HbF antigens. The labeled cells were analyzed by Bectin Dickerson LSR-II flow cytometer (BD Bioscience). All experiments were performed in triplicate.

Intravitreal Injection

HbAA- and HbSS-expressing Townes humanized knock-in sickle cell disease mice (6 weeks old; n=6) were used for intravitreal injection of MMF following our published protocol$_9$. Briefly, animals were weighed and anesthetized using 17 μL (1 μL/g body weight) of a solution of ketamine (80 mg/mL) and xylazine (12 mg/mL). Then 5 μL of proparacaine solution (5% w/v was administered topically to the eyes. MMF (1 μL; 10 mM solution prepared in PBS) was ten injected into the vitreous body of the right eye of each animal at the limbus; the left eye served as a contralateral control and received an equal volume of phosphate buffered saline (PBS, 0.01 M pH 7.4). Taking into account a total estimated vitreous volume of 10 μL per mouse eye, the final concentration of MMF achieved in our experimental system was 1 mM. At 24 h postinjection, mice were sacrificed via CO$_2$ inhalation, and eyes were harvested. Some eyes (n=3 per treatment group) were flash frozen in liquid nitrogen and cryosectioned for use in immunofluorescence analyses while the remaining were dissected to isolate RPE/eyecup from neural retina and total RNA prepared.

Results

Figures 7A, 7B, 7C, 7D, 7E:
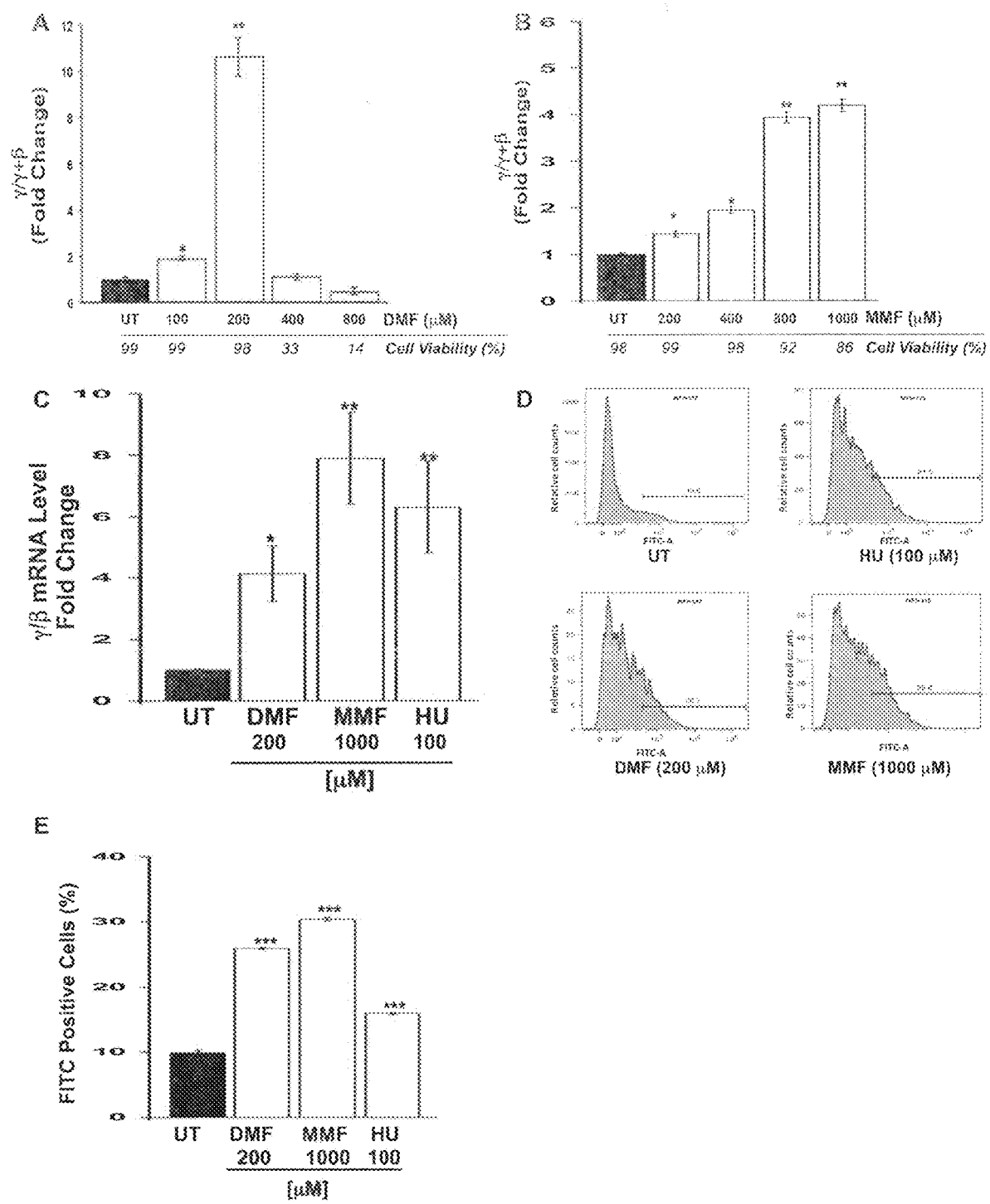
FIGS. 7A-7E show the induction of γ-globin gene expression and HbF production by dimethylfumarate (DMF) and monomethylfumarate (MMF) in erythroid cells. The dual luciferase reporter KU812 stable cell line ($1\times10^6$ cells/assay) was treated with varying concentrations (0-1000 μM) of DMF 7A or MMF 7B for 48 h. Cells cultured in the absence of the drugs were included as controls (UT, untreated). Firefly luciferase and renilla luciferase activity was measured for γ-globin and β-globin promoter activity, respectively. Trypan blue excursion was used to monitor cell viability.
Figure 9:
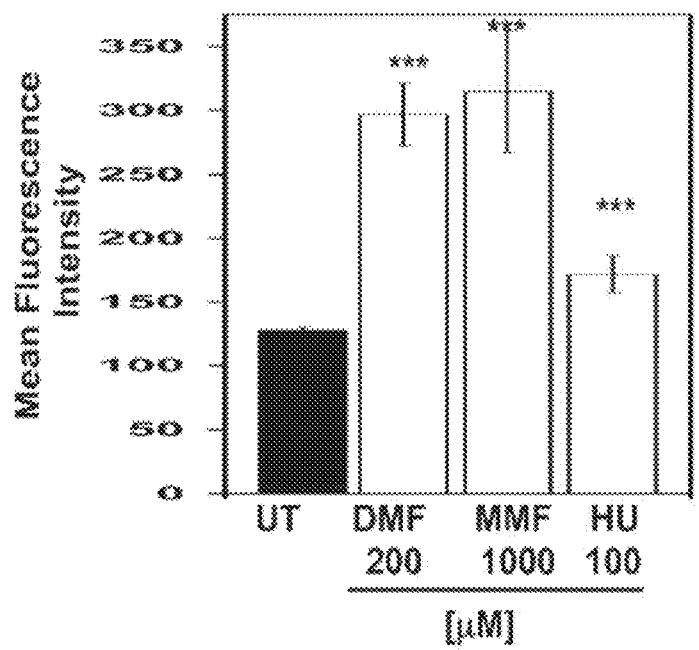
FIG. 9 is a bar graph showing FACS analysis of HbF protein expression. The graph shows Mean Fluorescence Intensity of primary human erythroid progenitor cells treated with 200 μM DMF, 1000 μM MMF, or 100 μM HU, (UT, untreated). ***$p<0.001$ compared to untreated control.
Figure 10:
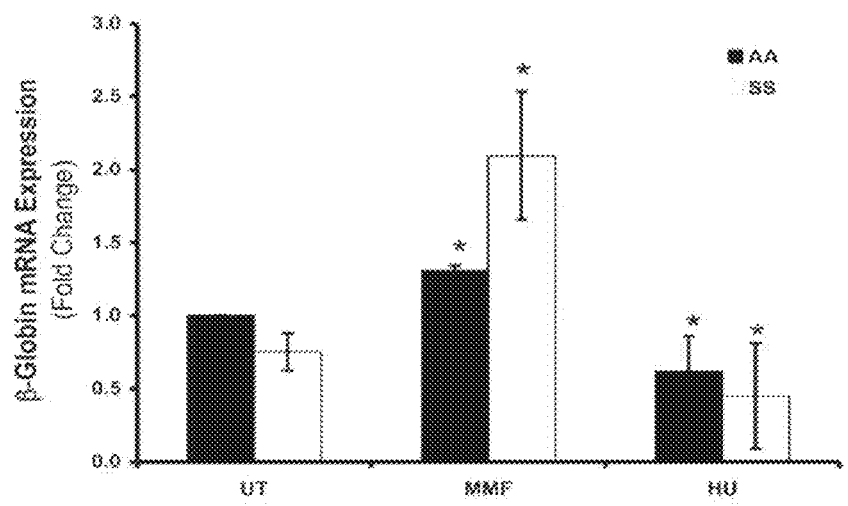
FIG. 10 is a bar graph showing β-Globin expression in AA and SS primary RPE. The expression of human β-globin mRNA (Fold Change) relative to that of hypoxanthine guanine phosphoribosyl transferase I (internal control) was analyzed by qPCR in AA (solid bar) and SS (open bar) primary RPE cells treated (24 h) with MMF (1000 μM) or HU (100 μM); UT, untreated control. *$p<0.05$ compared to respective untreated control.

Pharmacologic induction of HbF remains the best treatment approach to ameliorate the clinical complications of SCD. The pleiotropic actions of FAE in a broad spectrum of tissues, high tolerability and oral bioavailability, and recent FDA approval of Tecfidera (BG-12; Biogen Idec, Weston, Mass.) for use in multiple sclerosis make these agents attractive for rapid extrapolation to clinical trials in SCD. Therefore, the ability of DMF and MMF to induce γ-globin expression and HbF production in erythroid cells was investigated. The induction of γ-globin promoter activity by DMF and MMF was observed in KU812 cells by dual luciferase assay with maximal induction at 200 μM for DMF and 1000 μM MMF (FIGS. 7A and 7B); findings were confirmed in primary human erythroid cells (FIGS. 7C-7E). Levels of γ/β-globin mRNA were induced significantly by both DMF and MMF (4- and 8-fold, respectively; FIG. 7C). FACS demonstrated a 28- and 32-fold increase in HbF positive cells in the presence of these compounds (FIGS. 7D(1)-7D(4) and 7E), which is significantly higher than levels produced by HU (15-fold); see also FIG. 9. HbF protein expression was confirmed by Western blot (data not shown).

HbF protein production in ARPE-19 cells exposed to MMF (1000 µM) for 24 h was evaluated using a FITC-conjugated HbF antibody and fluorescence microscopy (data not shown). Cell nuclei were counterstained with DAPI. Treatments identical to those detailed above were performed using primary RPE cells isolated from the eyes of HbAA- or HbSS-expressing Townes humanized knock-in sickle cell disease mice and the expression of γ-globin mRNA evaluated by qPCR using primer pairs specific to the human γ-globin gene.

Data (mean±SEM) are from at least five data points generated from at least three independent drug treatments. For in vivo studies, six animals were included per group and samples were run in duplicate. Paired student t-test was performed and a P<0.05 was considered significant.

These data demonstrate the ability of DMF and MMF to induce HbF synthesis in human erythroid progenitors and support further testing in a pre-clinical sickle cell mouse model.

Figures 8A, 8B, 8C, 8D, 8E, 8F:
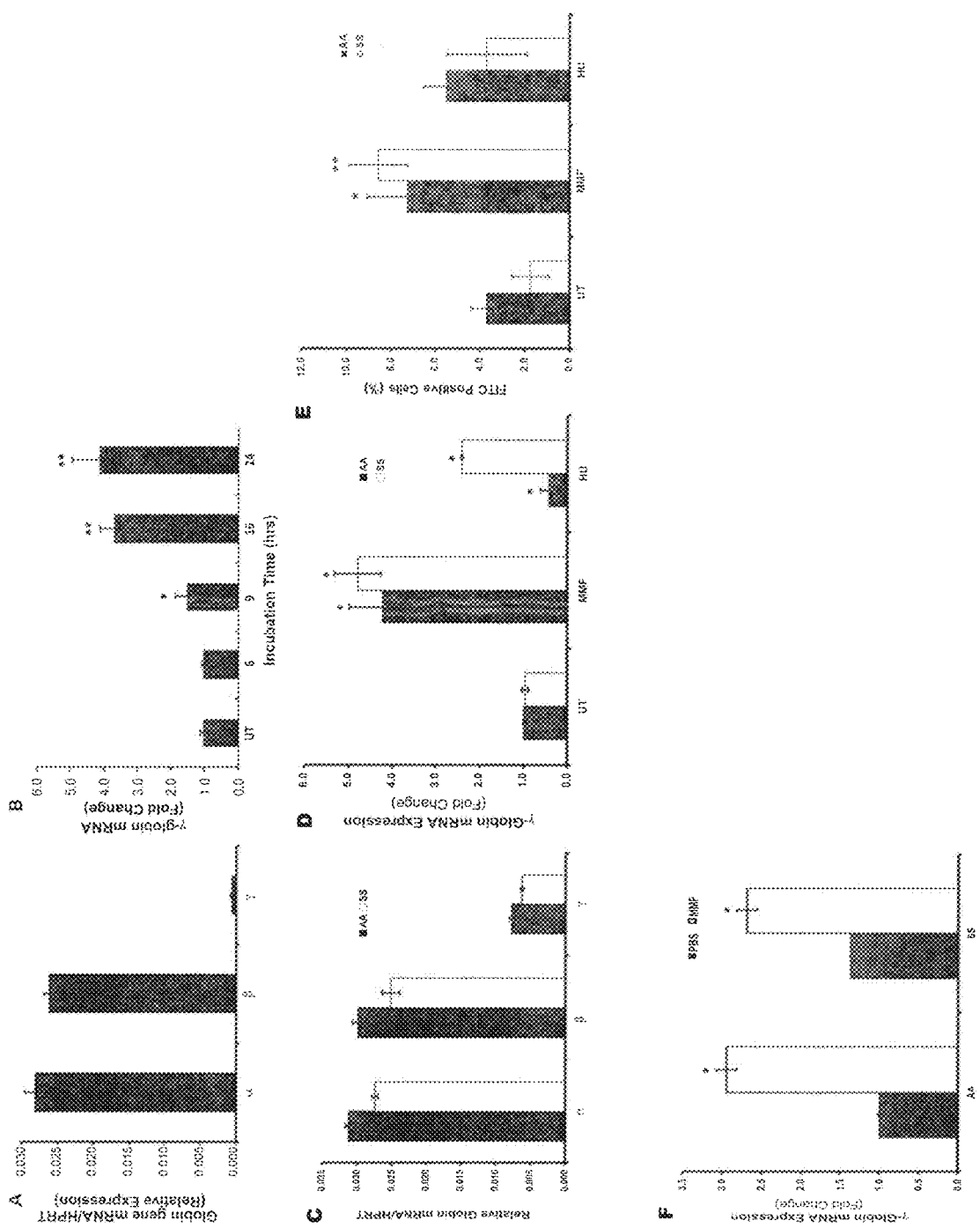
FIGS. 8A-8F are bar graphs showing globin gene expression and HbF production in human RPE cells.
Figure 8G:
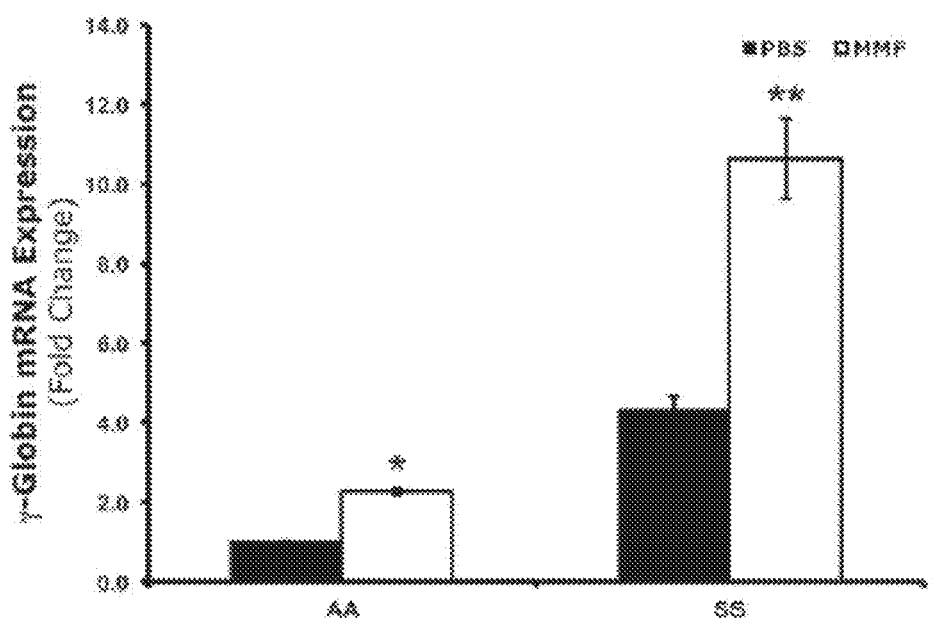
FIG. 8G is a bar graph of γGlobin mRNA Expression (Fold Change) in AA and SS cells treated with 0.01 M PBS pH7.4 (solid bars) or 1 mM final concentration of MMF (open bars).

Following oral intake, DMF is not detectable in plasma as it is rapidly hydrolyzed and converted into MMF. Based on this information, only MMF for studies with RPE cells were used (FIGS. 8A-8G). Findings in ARPE-19 and primary RPE cells mirrored closely those obtained in primary erythroid progenitors. This work confirms a single prior report of β-globin gene expression in RPE14 (FIGS. 8A and C) and demonstrates for the first time the induction of γ-globin expression and HbF production in these cells by MMF and HU (FIGS. 8B, 8D, 8E and FIG. 11). These data are further supported by in vivo studies demonstrating the significant elevation of γ-globin mRNA and HbF protein in RPE/eyecup and neural retina isolated from the eyes of HbAA and HbSS mice injected intravitreally with MMF (FIGS. 8F and 8G).

Though SR is thought to be largely a vascular disease, there is clinical evidence of early, non-vascular cell involvement, specifically of photoreceptor cell (PRC) dysfunction. PRCs, first order neurons in the visual pathway, have a high oxygen demand. Given their isolation from a vascular supply, they depend solely upon RPE cells for metabolic support. The synthesis of Hb by non-erythroid cells has been reported at other interfaces where $O_2/CO_2$ diffusion occurs; this may also be the case in RPE cells. The physiological importance of Hb production in RPE is yet to be determined; it is possible that defects in RPE Hb expression may contribute to retinal dysfunction and degeneration in SCD3.

Little is known regarding the impact of HbF-inducing therapies in the retina. A recent study by Estepp et al. demonstrated an inverse correlation between SR and plasma HbF concentration. Follow-up studies on a larger scale are required to substantiate HbF-inducing therapies to treat SR. Such therapy may confer benefit in patients of HbSS and HbSC genotypes, where the incidence of SR is highest. The present findings that FAE induce γ-globin expression and HbF production are new and support the possible re-purposing of BG-12 for treatment of SCD. Additionally, a new cellular target was identified for the therapeutic management of SR, a factor of high clinical relevance given the 10% incidence of vision loss and blindness among SCD patients and the lack of effective strategies for prevention and treatment.

Example 7: MMF Induces Expression of SLC22A4 (aka OCTN1)

Immunofluorescence analysis of human OCTN1 expression revealed the robust expression of the transporter in human primary erythroid cells generated in liquid culture from adult CD34+ stem cells.

Figure 11:
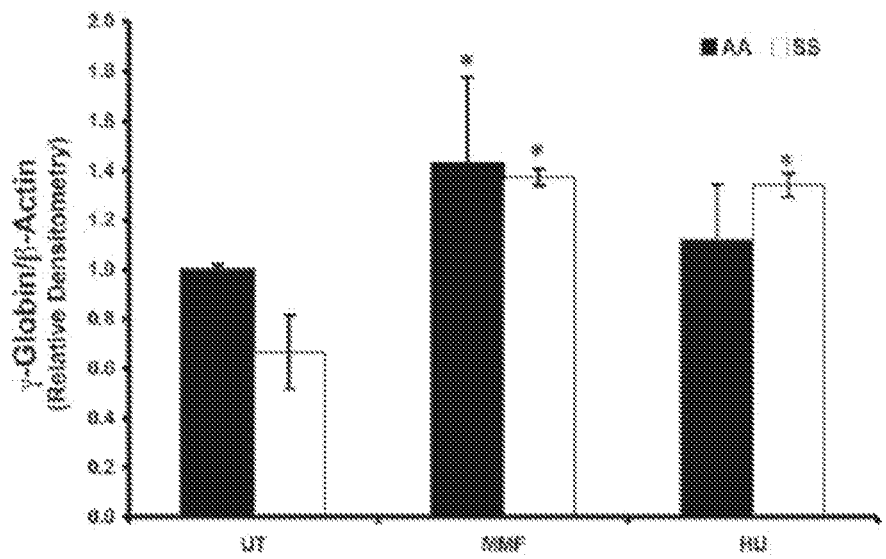
FIG. 11 is a bar graph showing the densitometeric analysis of a Western Blot analysis of HbF protein expression in AA and SS primary RPE. The graph is γ-Globin/β-Actin (Relative Densitometry) in cells treated with MMF or HU. (UT, untreated).

KU812, a human leukemic cell line that expresses the fetal γ-globin and adult β-globin genes, is a commonly used system for screening and discovery of novel HbF inducers (see above). FIG. 7 shows the robust induction of γ-globin mRNA and HbF production in these cells by MMF. FIG. 11 shows OCTN1 expression is also induced in these cells by MMF treatment (MMF, 1000 µM, 16 h). Data are represented as mean±standard error of the mean; *p<0.05.

Figure 12:
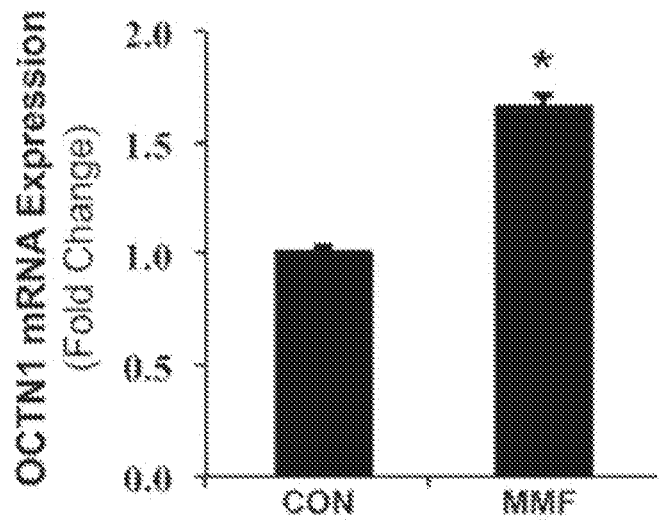
FIG. 12 is a bar graph of OCTN1 mRNA Expression (Fold Change) in KU812 cells treated with 1000 μM MMF for 16 hours. Control cells are identified as CON. Data are represented as mean±standard error of the mean; *$p<0.05$.

Red blood cells, cells of erythroid lineage, are the primary producers of hemoglobin. However, recent reports suggest other, nonhematopoietic cells to be capable of doing the same. The includes retinal pigment epithelial (RPE) cells, a cell type critical to normal visual function. FIG. 8 shows that induction of γ-globin gene expression and HbF protein production by MMF occurs in RPE. FIG. 12 shows that MMF also induces OCTN1 expression in these cells; HU alone had little to no effect on OCTN1 expression. Data are represented as mean±SEM; *p<0.05.

Figure 13:
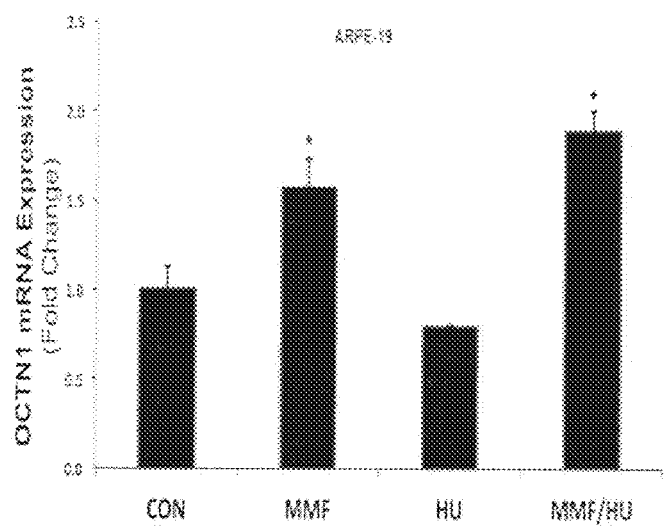
FIG. 13 is bar graph of OCTN1 mRNA Expression (Fold Change) in ARPE-19 cells treated with 1000 μM MMF, 100 μm HU, or 1000 μM MMF and 100 μM HU.

Example 8: MMF Induces OCTN1 mRNA and Protein Expression in Primary RPE Cells Isolated From HbAA- and HbSS-Expressing Mouse Retinas Given that ARPE-19 is a transformed human RPE cell line, the findings in RPE cells isolated freshly from the living animals as such cells was investigated to provide a more accurate representation of RPE cells in their native environment. Additionally, the humanized knock-in SCD mouse model (the Townes mouse), a rodent model engineered such that animals express human α, β, and γ globin rather than the rodent globin genes, allows for the pre-clinical study of parameters highly reflective of the human condition. The effects of MMF on OCTN1 expression in HbAA and HbSS-expressing primary RPE cells from this model was investigated. Treatment with 1000 µM MMF induced expression of OCTN1 robustly both at the RNA and protein level. (FIG. 13, *p<0.001).

Figure 14:
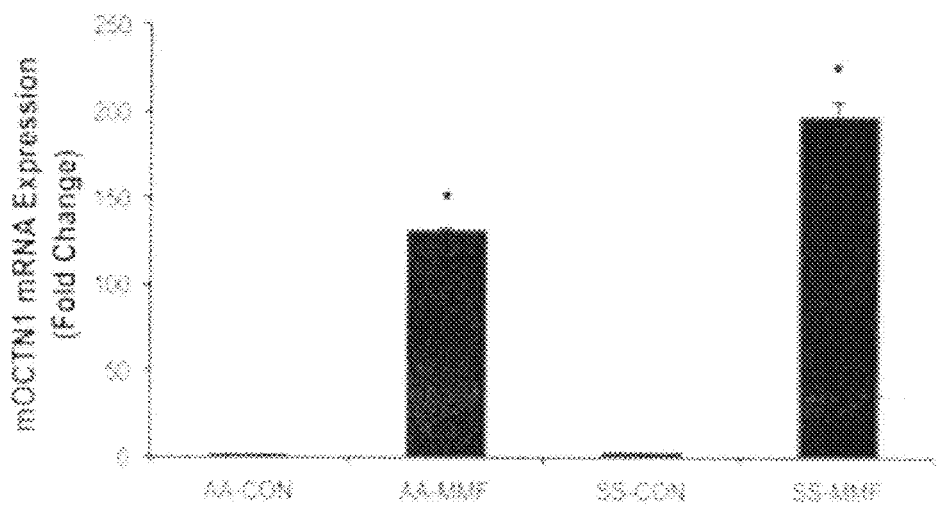
FIG. 14 is a bar graph of mOCTN1 mRNA expression (Fold Change) in AA or SS cells treated with 1000 μM MMF.
Figure 15:
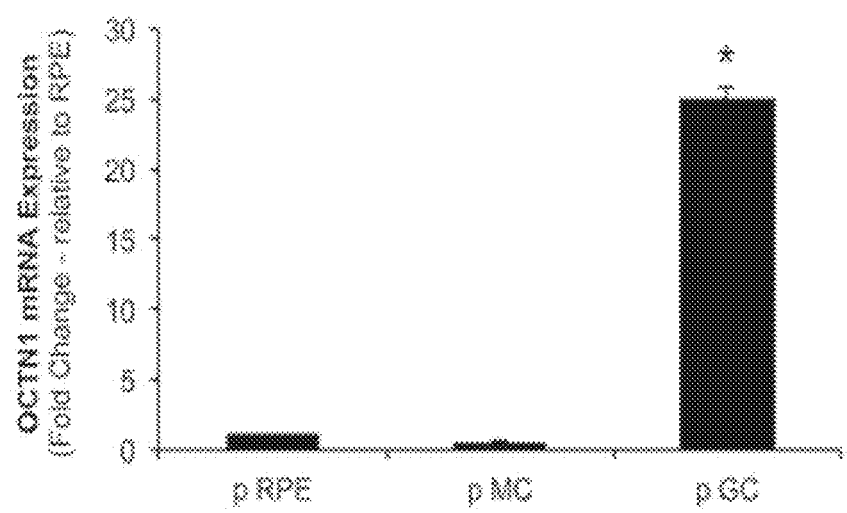
FIG. 15 is a bar graph of OCTN1 mRNA expression (Fold Change) in primary mouse RPE (pRPE), Muller (pMC) and ganglion (pGC) cells.

Example 9: MMF Induces OCTN1 Protein Expression In Vivo in HbAA- and HbSS-Expressing Mouse Retinas To determine whether the findings obtained in isolated retinal cells can be extrapolated to the in vivo condition, MMF (1 mM final concentration) was delivered intravitreally into the eyes of HbAA- and HbSS-expressing mice. 24 h post-injection, animals were sacrificed and OCTN1 expression evaluated by immunofluorescence. OCTN1 protein expression was upregulated throughout the entire retina (FIG. 14). Given that these animals are of a pigmented background and RPE is loaded with melanin pigment, a property that may interfere or mask fluorescent signal intensity, the expression of OCTN1 in the RPE cell layer specifically is not as apparent using this method. However, based upon data in primary RPE cells isolated from these animals (FIG. 13), it is upregulated in the RPE cell layer. It is important to note also, the expression of OCTN1 in other retinal regions namely, the retinal ganglion cell (rgc) layer and, the filamentous labeling from the rgcs to outer nuclear layer (onl), a pattern of localization consistent with the labeling of Muller cells. These data are congruent with our previous analysis of HbF protein expression, evaluated using immunofluorescence in similar cryosections, which revealed the MMF-induced upregulation of HbF in the RPE cell layer and throughout the neural retina (see FIG. 8).

qPCR analysis of OCTN1 mRNA expression in primary RPE, Muller and ganglion cells isolated from normal mouse retinas revealed expression of OCTN1 all three retinal cell types (FIG. 15). Interestingly, OCTN1 expression appeared to be highest in pGC's. The axons of the GC's communicate directly with the brain for higher visual processing/enabling of sight as they actually bundle as they exit retina to form the optic nerve. In keeping with this, an increase in OCTN1 expression and likely also HbF protein induced by MMF in these cells would be highly beneficial in protecting these neurons from the damaging effects of hypoxia, oxidative stress and inflammation produced characteristically in sickle cell disease.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the an will recognize, or be able to ascertain using no more than routine experimentation, many equivalents to the specific embodiments of the invention described herein. Such equivalents are intended to be encompassed by the following claims.

We claim:

1. A method for treating a hemoglobinopathy, a sickle cell-related disorder, or a beta thalassemia in a subject in need thereof, comprising administering to the subject a therapeutically effective amount of dimethylfumarate.

2. The method of claim 1, which is a method for treating a hemoglobinopathy.

3. The method of claim 2, wherein the hemoglobinopathy is a sickle cell disorder.

4. The method of claim 3, wherein the sickle cell disorder is sickle cell anemia.

5. The method of claim 1, which is a method for treating a beta thalassemia.

6. The method of claim 1, which is a method for treating a sickle cell-related disorder.

7. The method of claim 6, wherein the sickle cell-related disorder is a retinopathy.

8. The method of claim 1, wherein the method further comprises administering hydroxyurea to the subject.

9. The method of claim 8, wherein the subject is unresponsive to treatment with hydroxyurea alone.

10. The method of claim 9, wherein the subject expresses lower levels of OCTN1 than patients who respond to hydroxyurea.

11. The method of any one of claims 1-10, wherein the administering of the dimethylfumarate is orally.

12. The method of claim 7, wherein the administering of the dimethylfumarate is locally to the eye.

* * * * *